US012253583B2

(12) United States Patent
Xu et al.

(10) Patent No.: US 12,253,583 B2
(45) Date of Patent: Mar. 18, 2025

(54) COIL ASSEMBLY AND MAGNETIC RESONANCE SYSTEM

(71) Applicant: SHANGHAI UNITED IMAGING HEALTHCARE CO., LTD., Shanghai (CN)

(72) Inventors: Feng Xu, Shanghai (CN); Wei Luo, Shanghai (CN); Fuyi Fang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 173 days.

(21) Appl. No.: 17/660,026

(22) Filed: Apr. 21, 2022

(65) Prior Publication Data

US 2022/0349965 A1    Nov. 3, 2022

(30) Foreign Application Priority Data

Apr. 28, 2021   (CN) .......................... 202120895144.3
May 10, 2021   (CN) .......................... 202110505951.4
May 12, 2021   (CN) .......................... 202121010464.2

(51) Int. Cl.
*G01R 33/3415*   (2006.01)
*A61B 5/055*   (2006.01)
*G01R 33/36*   (2006.01)

(52) U.S. Cl.
CPC .......... *G01R 33/3415* (2013.01); *A61B 5/055* (2013.01); *G01R 33/3642* (2013.01); *G01R 33/3692* (2013.01)

(58) Field of Classification Search
CPC ............ G01R 33/3415; G01R 33/3642; G01R 33/3692; A61B 5/055
See application file for complete search history.

(56) References Cited

U.S. PATENT DOCUMENTS

| | | | |
|---|---|---|---|
| 6,535,084 B1* | 3/2003 | Tropp | H01P 7/00 324/318 |
| 10,024,934 B2 | 7/2018 | Harvey | |
| 2006/0012370 A1* | 1/2006 | Barberi | G01R 33/34046 324/318 |
| 2006/0033497 A1 | 2/2006 | Chmielewski et al. | |

(Continued)

FOREIGN PATENT DOCUMENTS

| | | |
|---|---|---|
| CN | 107632278 A | 1/2018 |
| CN | 208488538 U | 2/2019 |

(Continued)

OTHER PUBLICATIONS

Partial Supplementary European Search Report in European Application No. 22170477.8 mailed on Sep. 22, 2022, 13 pages.

*Primary Examiner* — Chao Sheng
(74) *Attorney, Agent, or Firm* — METIS IP LLC

(57) ABSTRACT

The present disclosure may provide a coil assembly. The coil assembly may include a supporting assembly and a radio frequency (RF) coil supported on the supporting assembly. The RF coil may have a plurality of coil units and a plurality of transmission ports. At least one of the plurality of transmission ports may be operably connected to a single coil unit of the plurality of coil units. Each of the plurality of transmission ports may be configured to transmit a drive signal to one of the plurality of coil units for generating a magnetic field.

20 Claims, 13 Drawing Sheets

(56) References Cited

U.S. PATENT DOCUMENTS

| | | | |
|---|---|---|---|
| 2006/0158188 A1* | 7/2006 | Hudson | G01R 33/3635 |
| | | | 324/303 |
| 2010/0277168 A1 | 11/2010 | Luedeke | |
| 2013/0069652 A1 | 3/2013 | Otake et al. | |
| 2013/0165768 A1 | 6/2013 | Biber | |
| 2016/0131728 A1 | 5/2016 | Biber et al. | |
| 2018/0149719 A1 | 5/2018 | Han et al. | |
| 2018/0210046 A1 | 7/2018 | Xu | |
| 2018/0313918 A1* | 11/2018 | Yang | G01R 33/3875 |
| 2019/0079153 A1* | 3/2019 | Eberler | G01R 33/3642 |
| 2019/0227133 A1 | 7/2019 | Leussler et al. | |
| 2021/0059556 A1 | 3/2021 | Leussler et al. | |

FOREIGN PATENT DOCUMENTS

| | | |
|---|---|---|
| CN | 112162224 A | 1/2021 |
| JP | H08187235 A | 7/1996 |
| KR | 101819893 B1 | 1/2018 |

\* cited by examiner

COIL ASSEMBLY AND MAGNETIC RESONANCE SYSTEM

CROSS-REFERENCE TO RELATED APPLICATIONS

This application claims priority to Chinese Patent Application No. 202120895144.3, filed on Apr. 28, 2021, Chinese Patent Application No. 202110505951.4, filed on May 10, 2021, and Chinese Patent Application No. 202121010464.2, filed on May 12, 2021, the contents of each of which are hereby incorporated by reference.

TECHNICAL FIELD

The present disclosure generally relates to magnetic resonance (MR), and more particularly, relates to a coil assembly thereof.

BACKGROUND

Magnetic resonance imaging (MRI) may utilize interaction between magnetic fields (e.g., a main magnetic field ($B_0$), a magnetic field ($B_1$)) and nuclear spins inside an object (e.g., a patient) to generate an image of the object. To generate an MRI image, a radio frequency (RF) coil may generate a magnetic field ($B_1$) for exciting the nuclear spins inside an object. The quality of the image may be negatively affected by relatively row homogeneity of the magnetic field ($B_1$). Thus, it is desirable to design a coil assembly configured to generate a magnetic field ($B_1$) of relatively high homogeneity.

SUMMARY

According to one aspect of the present disclosure, a coil assembly may be provided. The coil assembly may include a supporting assembly and a radio frequency (RF) coil supported on the supporting assembly. The RF coil may have a plurality of coil units and a plurality of transmission ports. At least one of the plurality of transmission ports may be operably connected to a single coil unit of the plurality of coil units. Each of the plurality of transmission ports may be configured to transmit a drive signal to one of the plurality of coil units for generating a magnetic field.

In some embodiments, the plurality of transmission ports may be arranged along a circumferential direction of the RF coil or a circumferential direction of the supporting assembly.

In some embodiments, a plurality of electrical components may be supported on the supporting assembly. One of the plurality of electrical components may be operably connected to one of the plurality of transmission ports. The electrical component may be configured to generate the drive signal.

In some embodiments, the plurality of electrical components may be arranged along a circumferential direction of the RF coil or a circumferential direction of the supporting assembly.

In some embodiments, at least one of the plurality of electrical components may include a cable and a cable trap. A first end of the cable may be operably connected to one of the plurality of transmission ports for transmitting the drive signal. The cable trap may be configured to define a frequency of the drive signal.

In some embodiments, a second end of the cable may lead to a second transmission port. The second transmission port may be configured to transmit a power to the cable.

In some embodiments, a plurality of second transmission ports corresponding to the plurality of electrical components may be aggregated in a cable group. The cable group may be located on an end of the supporting assembly along an axial direction of the supporting assembly.

In some embodiments, a second electrical component may be configured for power supply of the RF coil. The second electrical component may include a second cable. A first end of the second cable may be operably connected to the RF coil. The second cable may be configured to transmit a signal for the power supply of the RF coil.

In some embodiments, a second end of the second cable and the second end of the cable may be on opposite ends along an axial direction of the supporting assembly.

In some embodiments, at least one tuning component may be located along a circumferential direction of the supporting assembly. The at least one tuning component may be configured to adjust a resonance frequency of the RF coil. At least one adjustment portion of the at least one tuning component may be located on a first end of the supporting assembly along an axial direction of the supporting assembly.

In some embodiments, at least one coupling component may be located along the circumferential direction of the supporting assembly. The at least one coupling component may be configured to adjust a coupling degree between the plurality of coil units. At least one adjustment portion of the at least one coupling component may be located on a second end of the supporting assembly along the axial direction of the supporting assembly.

In some embodiments, one of the at least one tuning component may include a tuning rod and a tuning capacitor.

In some embodiments, one of the at least one coupling component may include a coupling rod and a coupling capacitor.

In some embodiments, the supporting assembly may include at least one recess, and the at least one recess may be configured to accommodate at least one of the at least one tuning capacitor or the at least one coupling capacitor.

In some embodiments, the coil assembly may include a plurality of dielectric components located between an antenna of the RF coil and an object associated with coil assembly; and a plurality of accommodating components configured to support the plurality of dielectric components.

In some embodiments, a second supporting assembly may be located inside or outside the RF coil. The second supporting assembly may include a plurality of containers. The plurality of accommodating components may be located on the plurality of containers.

In some embodiments, at least a portion of the plurality of accommodating components may be employed for positioning the plurality of dielectric components based on a reference distribution of a reference aggregated magnetic field formed by a plurality of reference magnetic fields each of which is generated based on one of a plurality of reference coil units of a reference coil assembly.

In some embodiments, sizes of at least two of the plurality of coil units may be different.

In some embodiments, a size of each of the plurality of coil units may be set according to at least one of a distance between at least a portion of the coil unit and a portion of an object associated with the coil assembly or a reference distribution of a reference aggregated magnetic field formed by a plurality of reference magnetic fields each of which is generated based on one of a plurality reference coil units of a reference coil assembly.

According to another aspect of the present disclosure, a magnetic resonance system may be provided. The magnetic resonance system may include at least one coil assembly. Each of the at least one coil assembly may include: a supporting assembly and a radio frequency (RF) coil supported on the supporting assembly. The RF coil may have a plurality of coil units and a plurality of transmission ports. At least one of the plurality of transmission ports may be operably connected to a single coil unit of the plurality of coil units. Each of the plurality of transmission ports may be configured to transmit a drive signal to one of the plurality of coil units for generating a magnetic field.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
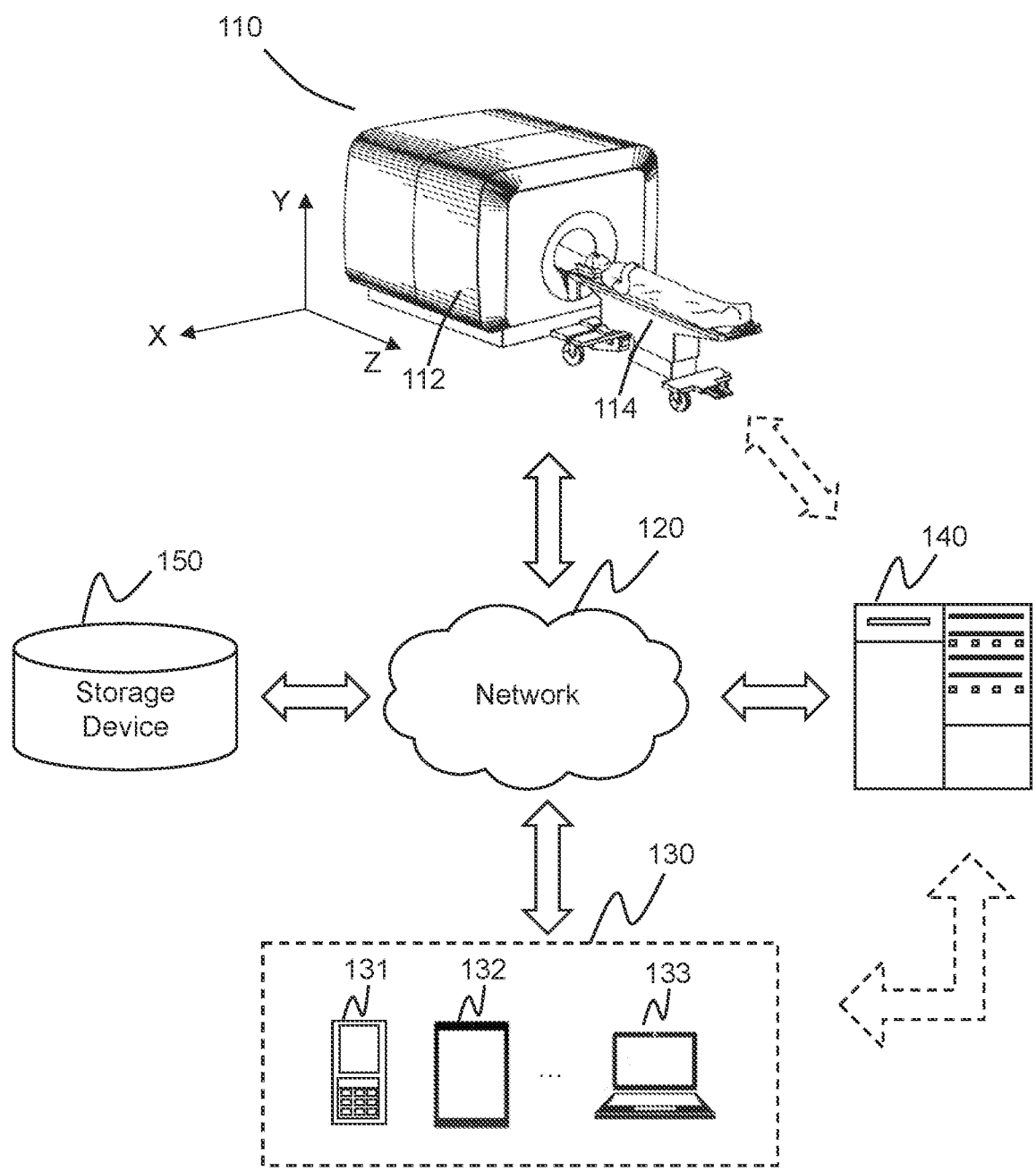
FIG. 1 is a schematic diagram illustrating an exemplary MRI system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

As used herein, the term "and/or" includes any and all combinations of one or more of the associated listed items.

In the present disclosure, unless otherwise expressly specified, the terms "mount," "connect," "couple," "fix," etc., should be understood in a broad sense, for example, it may be a fixed connection, a detachable connection, integrated into a whole, a mechanical connection, an electrical connection, directly connected, or indirectly connected via an intermediate medium, an internal connection of two elements, or an interconnection of two elements. For those skilled in the art, the specific meanings of the above terms in the present disclosure may be understood according to specific circumstances.

In the present disclosure, spatial reference terms such as "center," "longitudinal," "transverse," "length," "width," "thickness," "upper," "lower," "front," "back," "left," "right," "vertical," "horizontal," "top," "bottom," "inner," "outer," "clockwise," "counterclockwise," "axial," "radial," "circumferential," etc., indicate, in a relative sense, an orientation or positional relationship between two or more elements, assemblies, devices, or systems based on an orientation or positional relationship as shown in the drawings, and are only for the convenience and simplicity of description, rather than indicating or implying that the elements, assemblies, devices, or systems in the present disclosure have a particular orientation when the disclosed system, or a portion thereof, is in operation, or are constructed and operated in a particular orientation, and therefore should not be understood as a limitation of the present disclosure.

In the present disclosure, unless expressly stated otherwise, a first feature being "above" or "below" a second feature may be that the first feature and the second feature are in direct contact, or the first feature and the second feature may be in indirect contact via an intermediate medium. In some embodiments, the first feature being "above" or "on" the second feature may mean that the first feature is directly above or obliquely above the second feature, or simply mean that a horizontal height of the first feature is higher than a horizontal height of the second feature. The first feature being "below" or "underneath" the second feature may mean that the first feature is directly below or obliquely below the second feature, or it may simply mean that a horizontal height of the first feature is smaller than a horizontal height of the second feature.

It will be understood that, although the terms "first," "second," "third," etc., may be used herein to distinguish one element from another. For example, a first element may be termed a second element, and similarly, a second element may be termed a first element, without departing from the scope of exemplary embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a magnetic resonance-computed tomography imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on an object. The treatment device may include an accelerator of species of particles including, for example, photons, electrons, protons, or heavy ions. The imaging device may include an MRI scanner.

According to some embodiments of the present disclosure, a coil assembly may be provided. The coil assembly may be configured to generate a magnetic field ($B_1$). The magnetic field ($B_1$) may be applied to excite nuclear spins inside an object (e.g., a patient), and an image of the object may be generated based on a magnetic resonance (MR) signal determined based on the nuclear spins. The object may be placed in a cavity of the coil assembly; that is, the coil assembly may surround the object. In some embodiments, the coil assembly may have a plurality of coil units (e.g., a plurality of loops). The plurality of coil units may be configured so as to improve the homogeneity of the magnetic field ($B_1$). For instance, sizes of at least two of the plurality of coil units may be different. In some embodiments, a size of each of the plurality of coil units may be set according to at least one of a reference distribution of a reference magnetic field generated by a reference coil assembly or a distance between at least a portion of the coil unit and a portion at issue of the object. The reference coil assembly may be the same as or similar to the coil assembly except that the reference coil assembly includes the plurality of coil units of a same size.

Alternatively or additionally, the coil assembly may include a supporting assembly (e.g., a hollow cylinder) and an RF coil. The RF coil may be supported on the supporting assembly. The RF coil may have a plurality of coil units and a plurality of transmission ports (e.g., 8 transmission ports). At least one of the plurality of transmission ports may be operably connected to a single coil unit of the plurality of coil units. Each of the plurality of transmission ports may be configured to transmit a drive signal to one of the plurality of coil units for generating a magnetic field. In such cases, the coil assembly may generate an aggregated magnetic field ($B_1$) formed by a plurality of magnetic fields each of which is generated based on one of the plurality of coil units. An adjustment of at least one of the plurality of coil units may lead to an adjustment of the homogeneity of the aggregated magnetic field ($B_1$). Accordingly, the homogeneity of the aggregated magnetic field ($B_1$) may be flexibly adjusted.

Alternatively or additionally, the coil assembly may include an RF coil and a plurality of dielectric components. The RF coil may be configured to generate a magnetic field ($B_1$). The magnetic field ($B_1$) may be applied to excite nuclear spins inside an object (e.g., a patient), and an image of the object may be generated based on an MR signal determined based on the nuclear spins. The object may be placed in a cavity of the RF coil; that is, the RF coil may surround the object. The plurality of dielectric components may be positioned inside or outside the RF coil. In some embodiments, the coil assembly may also include a plurality of accommodating components configured to accommodate the plurality of dielectric components, respectively. In order to improve the homogeneity of the magnetic field ($B_1$), at least a portion of the plurality of accommodating components may be employed for positioning the plurality of dielectric components based on a reference distribution of a reference magnetic field generated by a reference coil assembly. The reference coil assembly may be the same as or similar to the coil assembly except that the reference coil assembly includes no dielectric component.

It should be noted that the above descriptions are non-limiting. Various features of the coil assembly described herein may be employed individually or in a combination so as to improve the homogeneity of a magnetic field ($B_1$). For example, the coil assembly may include a plurality of coil units of different sizes and a plurality of transmission ports. As another example, the coil assembly may include a plurality of coil units of different sizes and a plurality of dielectric components. As a further example, the coil assembly may include a plurality of transmission ports and a plurality of dielectric components. As still a further example, the coil assembly may include a plurality of coil units of different sizes, a plurality of transmission ports, and a plurality of dielectric components.

FIG. 1 is a schematic diagram illustrating an exemplary MRI system 100 according to some embodiments of the present disclosure. As illustrated, the MRI system 100 may include an MRI scanner 110, a network 120, a terminal 130, a processing device 140, and a storage device 150. The components of the MRI system 100 may be connected in one or more of various ways. Merely by way of example, as illustrated in FIG. 1, the MRI scanner 110 may be connected to the processing device 140 through the network 120. As another example, the MRI scanner 110 may be connected to the processing device 140 directly (as indicated by the bi-directional arrow in dotted lines linking the MRI scanner 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

The MRI scanner 110 may scan an object located within its detection region and generate data relating to the object. In the present disclosure, "subject" and "object" are used interchangeably. Merely by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof. In some embodiments, the MRI scanner 110 may be a close-bore scanner or an open-bore scanner.

In the present disclosure, the X-axis, the Y-axis, and the Z-axis shown in FIG. 1 may form an orthogonal coordinate system. The X-axis and the Z-axis shown in FIG. 1 may be horizontal, and the Y-axis may be vertical. As illustrated, the positive X-direction along the X-axis may be from the right side to the left side of the MRI scanner 110 seen from the direction facing the front of the MRI scanner 110; the positive Y-direction along the Y-axis shown in FIG. 1 may be from the lower part to the upper part of the MRI scanner 110; the positive Z-direction along the Z-axis shown in FIG. 1 may refer to a direction in which the object is moved out of the detection region (or referred to as the bore) of the MRI scanner 110. More descriptions of the MRI scanner 110 may be found elsewhere in the present disclosure. See, e.g., FIG. 2 and the description thereof.

In some embodiments, the MRI scanner 110 may include a gantry 112 and a patient support 114 (e.g., along the Z-direction). In some embodiments, the gantry 112 may be configured to support magnets (e.g., the main magnet 201 in FIG. 2), coils (e.g., the gradient coils 202 and/or the radio frequency (RF) coils 203 in FIG. 2), etc. The gantry 112 may surround, along the Z-direction, the object that is moved into or located within the detection region. In some embodiments, the patient support 114 may be configured to support the object. In some embodiments, the patient support 114 may have 6 degrees of freedom, for example, three translational degrees of freedom along three coordinate directions (i.e., X-direction, Y-direction, and Z-direction) and three rotational degrees of freedom around the three coordinate directions. Accordingly, the object may be positioned by the patient support 114 within the detection region. Merely by way of example, the patient support 114 may move the object into the detection region along the Z-direction in FIG. 1.

The network 120 may include any suitable network that can facilitate the exchange of information and/or data for the MRI system 100. In some embodiments, one or more components of the MRI system 100 (e.g., the MRI scanner 110, the terminal 130, the processing device 140, or the storage device 150) may communicate information and/or data with one or more other components of the MRI system 100 via the network 120. For example, the processing device 140 may obtain signals of an RF pulse from the MRI scanner 110 via the network 120. In some embodiments, the network 120 may be any type of wired or wireless network, or a combination thereof.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the terminal 130 may remotely operate the MRI scanner 110 and/or the processing device 140. In some embodiments, the terminal 130 may operate the MRI scanner 110 and/or the processing device 140 via a wireless connection. In some embodiments, the terminal 130 may receive information and/or instructions inputted by a user, and send the received information and/or instructions to the MRI scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the MRI scanner 110, the terminal 130, and/or the storage device 150. For example, the processing device 140 may process an MR signal generated by the MRI scanner 110 and encode the MR signal for generating an image. In some embodiments, the processing device 140 may be a single server, or a server group. The server group may be centralized or distributed. In some embodiments, the processing device 140 may be local or remote. In some embodiments, the processing device 140 may be implemented on a cloud platform.

The storage device 150 may store data and/or instructions. In some embodiments, the storage device 150 may store data obtained from the MRI scanner 110, the terminal 130 and/or the processing device 140. For example, the storage device 150 may store an MR signal generated by the MRI scanner 110. In some embodiments, the storage device 150 may store data and/or instructions that the processing device 140 may execute or use to perform exemplary methods described in the present disclosure. For example, the storage device 150 may store instructions that the processing device 140 may execute to process an MR signal generated by the MRI scanner 110 and encode the MR signal for generating an image. In some embodiments, the storage device 150 may include a mass storage device, a removable storage device, a volatile read-and-write memory, a read-only memory (ROM), or the like, or any combination thereof. In some embodiments, the storage device 150 may be implemented on a cloud platform.

In some embodiments, the storage device 150 may be connected to the network 120 to communicate with one or more components of the MRI system 100 (e.g., the MRI scanner 110, the processing device 140, the terminal 130, etc.). One or more components of the MRI system 100 may access the data or instructions stored in the storage device 150 via the network 120. In some embodiments, the storage device 150 may be part of the processing device 140.

In some embodiments, the MRI system 100 may further include one or more power supplies (not shown in FIG. 1) operably connected to one or more components of the MRI system 100 (e.g., the MRI scanner 110, the processing device 140, the terminal 130, the storage device 150, etc.).

Figure 2:
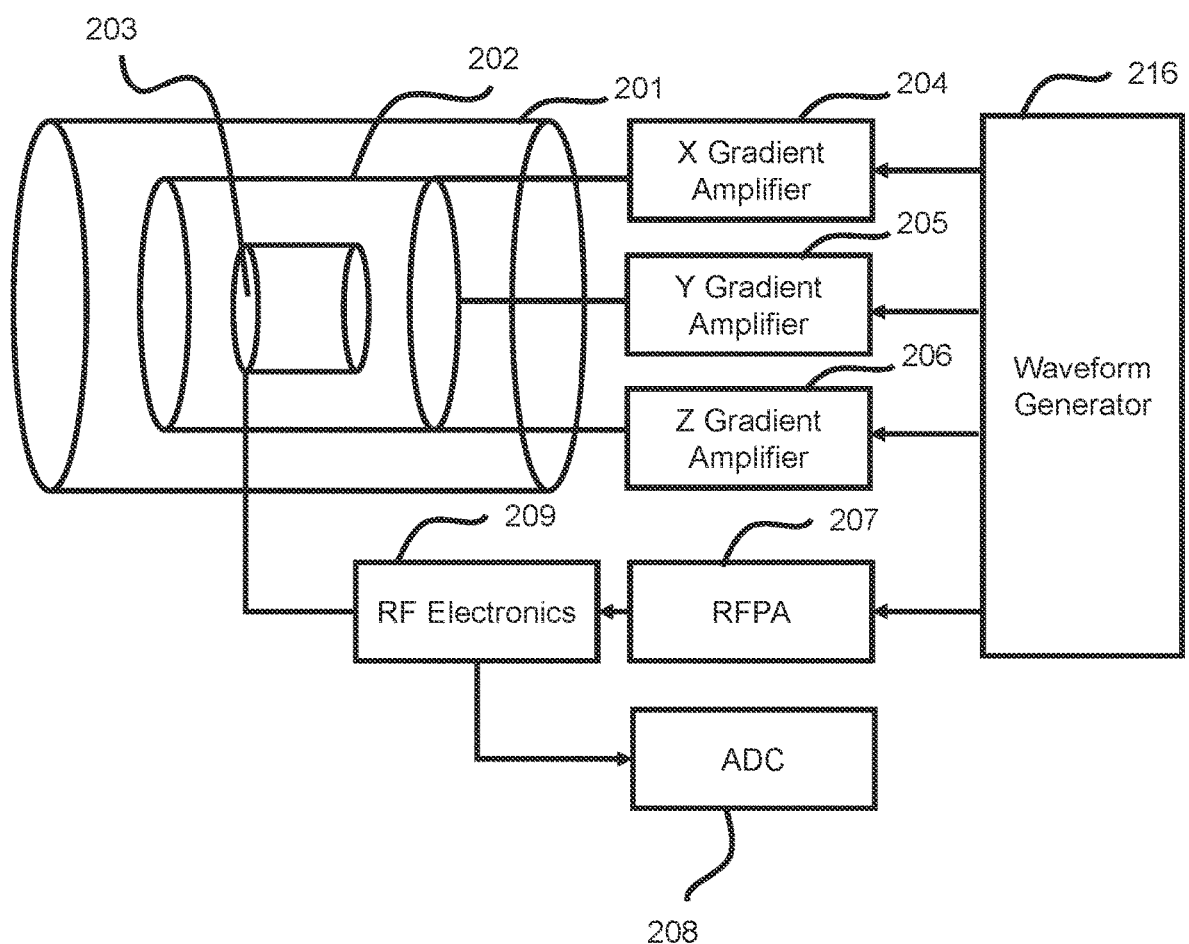
FIG. 2 is a schematic diagram illustrating an exemplary MRI scanner according to some embodiments of the present disclosure.

FIG. 2 is a schematic diagram illustrating an exemplary MRI scanner according to some embodiments of the present disclosure.

As illustrated, the main magnet 201 may generate a first magnetic field (or referred to as a main magnetic field) that may be applied to an object (also referred to as a subject) positioned inside the first magnetic field. The main magnet 201 may include a resistive magnet or a superconductive magnet that both need a power supply (not shown in FIG. 2) for operation. Alternatively, the main magnet 201 may include a permanent magnet. The main magnet 201 may form the detection region and surround, along the Z-direction, the object that is moved into or positioned within the detection region. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply. In some embodiments, an intensity of the main magnet 201 may include 1.5 T, 3 T, 5 T, 7 T, 9 T, or more.

Gradient coils 202 may be located inside the main magnet 201. For example, the gradient coils 202 may be located in the detection region. The gradient coils 202 may surround, along the Z-direction, the object that is moved into or positioned within the detection region. The gradient coils 202 may be surrounded by the main magnet 201 around the Z-direction, and be closer to the object than the main magnet 201. The gradient coils 202 may generate a second magnetic field (or referred to as a gradient field, including gradient fields Gx, Gy, and Gz). The second magnetic field may be superimposed on the main magnetic field generated by the main magnet 201 and distort the main magnetic field so that the magnetic orientations of the protons of an object may vary as a function of their positions inside the gradient field, thereby encoding spatial information into MR signals generated by the region of the object being imaged. The gradient coils 202 may include X coils (e.g., configured to generate the gradient field Gx corresponding to the X-direction), Y coils (e.g., configured to generate the gradient field Gy corresponding to the Y-direction), and/or Z coils (e.g., configured to generate the gradient field Gz corresponding to the Z-direction) (not shown in FIG. 2). The three sets of coils may generate three different magnetic fields that are used for position encoding. The gradient coils 202 may allow spatial encoding of MR signals for image reconstruction. The gradient coils 202 may be connected to one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments, the X coils and Y coils may be energized to generate the gradient fields in the X-direction and the Y-direction. As used herein, the X-axis, the Y-axis, the Z-axis, the X-direction, the Y-direction, and the Z-direction in the description of FIG. 2 are the same as or similar to those described in FIG. 1.

In some embodiments, radio frequency (RF) coils 203 may be located inside the main magnet 201 and serve as transmitters, receivers, or both. For example, the RF coils 203 may be located in the detection region. The RF coils 203 may surround, along the Z-direction, the object that is moved into or positioned within the detection region. The RF coils 203 may be surrounded by the main magnet 201 and/or the gradient coils 202 around the Z-direction, and be closer to the object than the gradient coils 202. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the region of the object being imaged. Atoms (e.g., hydrogen atoms) inside the region of the object may absorb energy and produce resonance in response to the third magnetic field. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC

208. The ADC 208 may transform the MR signals from analog signals to digital signals. The digital MR signals then may be sent to the processing device 140 for sampling. In some embodiments, at least one switch component may be operably connected to the RF coils for facilitating the RF coils to switch between functioning as transmitters and as the receivers.

In some embodiments, an RF coil may have a cylindrical shape, a birdcage shape, a sheet shape, a stripline shape, a lattice shape, an elliptic shape, or the like, or any combination thereof. For example, the RF coil may include a volume transmit coil (VTC) having a cylindrical birdcage shape. As another example, the RF coil may include a transverse electromagnetic (TEM) coil having an elliptic shape.

In some embodiments, the main magnet 201, the gradient coils 202, and the RF coils 203 may be circumferentially positioned with respect to the object around the Z-direction. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA or a nonlinear RFPA. In some embodiments, the RFPA 207 may include one or more RFPAs.

In some embodiments of the present disclosure, a coil assembly may be configured to generate a magnetic field ($B_1$). The magnetic field ($B_1$) may be applied to excite nuclear spins inside an object (e.g., a patient), and an image of the object may be generated based on an MR signal determined based on the nuclear spins. The object may be placed in a cavity of the coil assembly; that is, the coil assembly may surround the object, for example, by 360 degrees. For example, the coil assembly may include a birdcage RF coil.

In some embodiments, the coil assembly may include an RF coil. The RF coil may have a plurality of coil units (e.g., a plurality of loops). In some embodiments, the plurality of coil units may be divided into a first coil portion, a second coil portion, and a plurality of third coil portions. In some embodiments, the plurality of third coil portions may be located between the first coil portion and the second coil portion. Each of the plurality of third coil portions may be connected to a position of the first coil portion and a position of the second coil portion, respectively. Accordingly, the plurality of third coil portions may divide the first coil portion into a plurality of first sections (e.g., 371, 372, 373, 374, 375, 376, 377, or 378 in FIG. 4 and FIG. 5) and divide the second coil portion into a plurality of second sections (e.g., 381, 382, 383, 384, 385, 386, 387, or 388 in FIG. 4 and FIG. 5), respectively. A first section between two adjacent third coil portions and a second section between the same two adjacent third coil portions, in combination with the two adjacent third coil portions, may form one of the plurality of coil units. As used herein, two third coil portions are considered adjacent if there is no other third coil portion of the same type and or structure positioned between the two third coil portions.

In some embodiments, the first coil portion may be in a first plane that is parallel with a second plane where the second coil portion is. Each of the plurality of third coil portions may have a long axis that is perpendicular to the first plane and the second plane. In some embodiments, a first section and a second section corresponding to a same coil unit may have a same length. In some embodiments, the first section and the second section corresponding to a same coil unit may have different lengths. In some embodiments, a cross-section of a third coil portion may have the shape of a strip, a circle, an ellipse, a polygon (e.g., a trapezoid, a rectangle, a triangle), or the like, or any combination thereof. A cross-section of the first coil portion or the second coil portion may have the shape of a circle, a polygon, an ellipse, etc. In some embodiments, a count of the plurality of third coil portions may be non-limiting, for example, 8, 9, 10, etc.

In some embodiments, the quality of an MR image may be affected by the homogeneity of the magnetic field ($B_1$). The homogeneity of the magnetic field ($B_1$) may be affected by at least one of various factors including, for example, an intensity of a main magnetic field ($B_0$), an imperfection of the coil assembly due to, e.g., an imperfect manufacturing process, etc. In some embodiments, the larger the intensity of the main magnetic field ($B_0$) is, the larger an operation frequency of the coil assembly may be, and the lower the homogeneity of the magnetic field ($B_1$) may be. In some cases, an existing coil assembly may include an RF coil having a plurality of coil units of a same size, where one or more of the various factors exemplified above that may lead to an inhomogeneous magnetic field ($B_1$) are ignored or not compensated, resulting in relatively low homogeneity of the magnetic field ($B_1$) generated by such a coil assembly. In order to solve the problems, according to some embodiments of the present disclosure, sizes of at least two of the plurality of coil units of the coil assembly may be set differently. As used herein, a size of a coil unit may refer to an area formed by a first section between two adjacent third coil portions, a second section between the same two adjacent third coil portions, and the two adjacent third coil portions. In some embodiments, the lengths of the plurality of third coil portions may be the same; accordingly, two coil units of different sizes may indicate that lengths of two first sections corresponding to the two coil units are different, and/or lengths of two second sections corresponding to the two coil units are different; two coil units of a same size may indicate that lengths of two first sections corresponding to the two coil units are the same, and lengths of two second sections corresponding to the two coil units are the same.

In some embodiments, a size of a coil unit of the plurality of coil units may be set according to a reference distribution of a reference magnetic field ($B_1$) generated by a reference coil assembly, a distance between at least a portion of the coil unit (e.g., two third coil portions corresponding to the coil unit) and a portion at issue of the object, different portions of the object to be imaged using the coil unit, etc. In some embodiments, the reference coil assembly may be the same as or similar to the coil assembly except that the plurality of coil units have a same size. For instance, the reference coil assembly may include an RF coil having the plurality of coil units of a same size. A remaining portion of the reference coil assembly may be the same as a corresponding portion of the coil assembly other than the RF coil of the coil assembly. The reference distribution of the reference magnetic field ($B_1$) may be predetermined by scanning a reference object (e.g., a phantom) using an MRI scanner having the reference coil assembly. In some embodiments, the larger a size of a coil unit is, the larger an intensity of a magnetic field generated by the coil unit may be. Therefore, a size of at least one of the plurality of coil units corresponding to a region of a relatively low intensity in the reference distribution of the reference magnetic field ($B_1$) may be larger than a size of at least one of the plurality of coil units corresponding to a region of a relatively high intensity in the reference distribution of the reference magnetic field ($B_1$), thereby improving the homogeneity of the magnetic field ($B_1$) generated by the coil assembly, which in turn may improve the quality of an MR image determined based on MR data acquired using the coil assembly.

In some embodiments, if the distance between the at least a portion of the coil unit and the portion of the object at issue is smaller than a distance threshold, the portion of the object at issue may interfere with the magnetic field ($B_1$), negatively affecting the homogeneity of the magnetic field ($B_1$). In order to improve the homogeneity of the magnetic field ($B_1$), the distance between the at least a portion of the coil unit and the portion of the object at issue may need to exceed or be equal to the distance threshold. Accordingly, the size of each of at least one of the plurality of coil units may be set according to the distance threshold.

In some embodiments, different portions of the object may have different rates of absorption of the magnetic field ($B_1$) due to, e.g., the type(s) of tissue in the different portions of the object. The size of each of at least one of the plurality of coil units may be set according to one or more different portions of the object that are located in a vicinity of the coil unit.

In some embodiments, the homogeneity of the magnetic field ($B_1$) may also be adjusted by adjusting at least one parameter of the first coil portion, the second coil portion, or the plurality of third coil portions. For example, the at least one parameter may include a width of each of at least one of the plurality of third coil portions. The larger the width of a third coil portion is, the higher the intensity of a magnetic field generated by a coil unit including the third coil portion may be.

Figure 4:
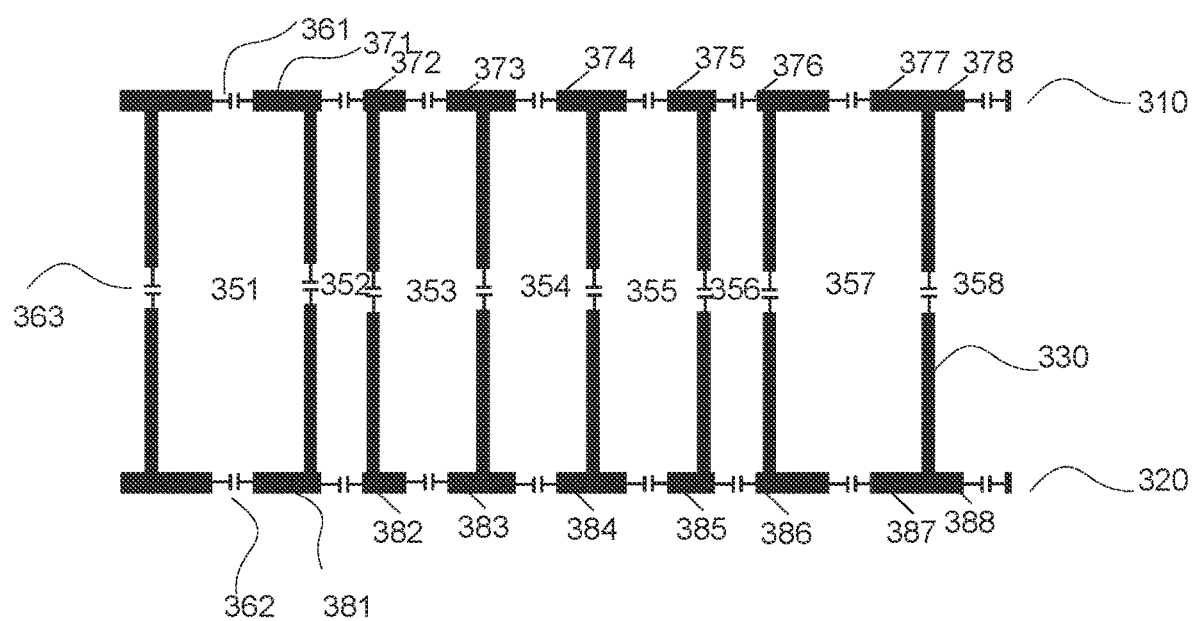
FIG. 4 is a schematic diagram illustrating a net of an exemplary assembly according to some embodiments of the present disclosure.
Figure 5:
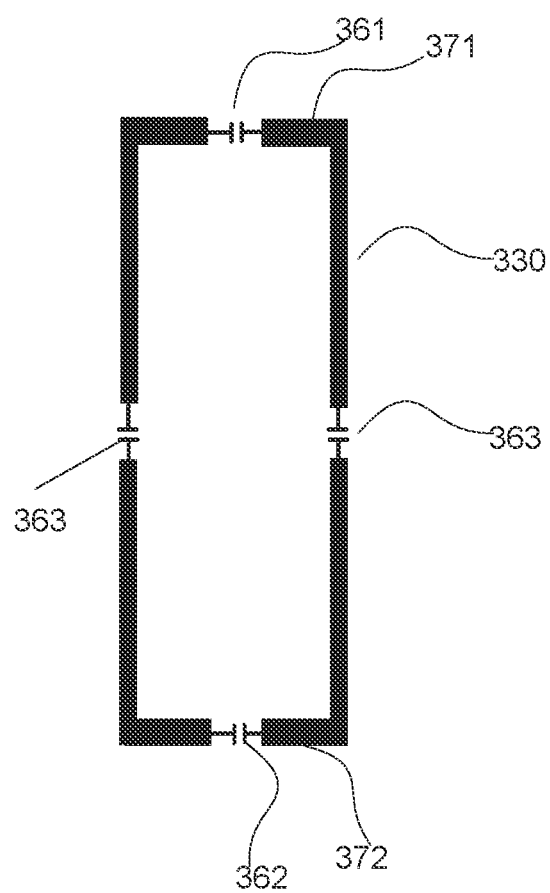
FIG. 5 is a schematic diagram illustrating an exemplary coil unit of an exemplary assembly according to some embodiments of the present disclosure.

In some embodiments, the first coil portion may include at least one first capacitor (e.g., 361 in FIG. 4 and FIG. 5). For example, the at least one first capacitor may include a plurality of first capacitors in series. At least one of the at least one first capacitor may be located on one of the plurality of first sections of the first coil portion. A count of the at least one first capacitor may be equal to or larger than a count of the plurality of first sections. In some embodiments, at least one capacitance of the at least one first capacitor may be the same. In some embodiments, the at least one capacitance of the at least one first capacitor may be different.

In some embodiments, the second coil portion may include at least one second capacitor (e.g., 362 in FIG. 4 and FIG. 5). For example, the at least one second capacitor may include a plurality of second capacitors in series. At least one of the at least one second capacitor may be located on one of the plurality of second sections of the second coil portion. A count of the at least one second capacitor may be equal to or larger than a count of the plurality of second sections. In some embodiments, the at least one second capacitor may include a plurality of second capacitors, and capacitances of all of the plurality of second capacitors may be the same. In some embodiments, at least two capacitances of at least two of the at least one second capacitor may be different. In some embodiments, the third coil portions may include at least one third capacitor (e.g., 363 in FIG. 4 and FIG. 5). Each of the plurality of third coil portions may include at least one of the at least one third capacitor. The at least one first capacitor, the at least one second capacitor, and the at least one third capacitor may be configured to reduce coupling between different coil units among the plurality of coil units. More descriptions of the coil assembly (e.g., the RF coil thereof) may be found elsewhere in the present disclosure. See, for example, FIG. 2 and the description thereof.

Figure 3:
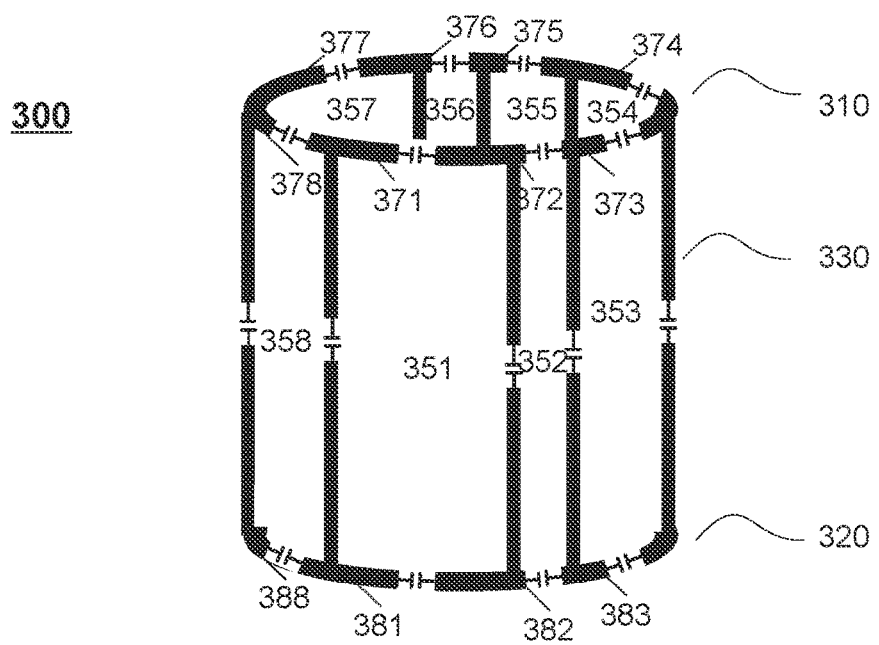
FIG. 3 is a stereogram illustrating an exemplary coil assembly according to some embodiments of the present disclosure.

FIG. 3 is a stereogram illustrating an exemplary coil assembly according to some embodiments of the present disclosure. FIG. 4 is a schematic diagram illustrating a net of the exemplary assembly according to some embodiments of the present disclosure. FIG. 5 is a schematic diagram illustrating an exemplary coil unit of the exemplary assembly according to some embodiments of the present disclosure.

As shown in FIGS. 3-5, the coil assembly 300 may include a first coil portion 310, a second coil portion 320, and 8 third coil portions 330, forming 8 coil units 351-358. The coil assembly 300 may be of a cylindrical birdcage configuration. As illustrated, two or more coil units of the coil assembly 300 may have a same dimension (also referred to as a same size). For instance, lengths of the first sections 371 and 377 corresponding to the first coil unit 351 and the seventh coil unit 357 and/or lengths of second sections 381 and 387 corresponding to the first coil unit 351 and the seventh coil unit 357 may have a first value; lengths of first sections 372 and 376 corresponding to the second coil unit 352 and the sixth coil unit 356 and/or lengths of second sections 382 and 386 corresponding to the second coil unit 352 and the sixth coil unit 356 may have a second value; lengths of first sections 373, 374, 375, and 378 corresponding to the third coil unit 353, the fourth coil unit 354, the fifth coil unit 355, and the eighth coil unit 358 and/or lengths of second sections 383, 384, 385, and 388 corresponding to the third coil unit 353, the fourth coil unit 354, the fifth coil unit 355, and the eighth coil unit 358 may have a third value. The first value may be larger than the second value, and the second value may be larger than the third value.

In some embodiments of the present disclosure, an MRI scanner may include a coil assembly. The coil assembly may include an RF coil. The RF coil may be configured to receive or emit an MR signal. The RF coil may include a first coil portion, a second coil portion, and a plurality of third coil portions. The first coil portion and the second coil portion may be spaced from each other. Ends of the plurality of third coil portions may be electrically connected to the first coil portion and the second coil portion, respectively, thereby forming a birdcage structure. The first coil portion, the second coil portion, and the plurality of third coil portions may form a plurality of coil units. Sizes of at least two of the plurality of coil units may be different. In some embodiments, the first coil portion may have at least one first capacitor. The second coil portion may have at least one second capacitor. The plurality of third coil portions may have at least one third capacitor. In some embodiments, the RF coil may be the same as or similar to the coil assembly 300 illustrated above, the descriptions of which are not repeated.

In some embodiments of the present disclosure, an MRI system may include the MRI scanner illustrated above. More descriptions of the MRI scanner and/or the MRI system may be found elsewhere in the present disclosure. See, for example, FIG. 1 and FIG. 2, and the descriptions thereof.

In some embodiments of the present disclosure, a coil assembly may include a supporting assembly (e.g., a hollow cylinder) and an RF coil. The RF coil may be supported on the supporting assembly. In some embodiments, the RF coil may surround the supporting assembly. An object may be placed inside a cavity of the supporting assembly, and an image of the object may be generated based on an MR signal determined by scanning the object. For example, the RF coil may include a body coil, a local coil, etc. As another example, the RF coil may include a birdcage coil (e.g., a degenerate birdcage coil (DBC)).

The RF coil may include a plurality of coil units (e.g., a plurality of loops). In some embodiments, the plurality of coil units of the RF coil may be divided into a first coil portion, a second coil portion, and a plurality of third coil portions. The first coil portion and the second coil portion may be located at an end of each of the plurality of third coil portions, respectively; that is, the plurality of third coil portions may be located between the first coil portion and the second coil portion. A third coil portion may be connected to a position of the first coil portion and a position of the second coil portion, respectively. Accordingly, the plurality of third coil portions may divide the first coil portion into a plurality of first sections and divide the second coil portion into a plurality of second sections. A first section between two adjacent third coil portions and a second section between the two adjacent third coil portions, in combination with the two adjacent third coil portions, may form one of the plurality of coil units.

In some embodiments, the plurality of third coil portions may be arranged along a circumferential direction of the RF coil or a circumferential direction of the supporting assembly. Accordingly, the plurality of coil units may be arranged along the circumferential direction of the RF coil or the circumferential direction of the supporting assembly. In some embodiments, a count of the plurality of coil units may be the same as a count of the plurality of third coil portions. In some embodiments, the RF coil may include an antenna and a conductor. The first coil portion, the second coil portion, and the plurality of third coil portions may be made of an electrically conductive material, for example, copper, forming the conductor. The antenna may be distributed on the first coil portion, the second coil portion, and/or the plurality of third coil portions.

In some embodiments, the RF coil may include a plurality of transmission ports. At least one of the plurality of transmission ports may be operably connected to a single coil unit of the plurality of coil units. In some embodiments, a count of the plurality of transmission ports may be the same as the count of the plurality of coil units or the count of the plurality of third coil portions. A transmission port may be configured to transmit a drive signal to one of the plurality of coil units for generating a magnetic field. The RF coil may generate an aggregated magnetic field formed by a plurality of magnetic fields each of which is generated based on one of the plurality of coil units. In some embodiments, the plurality of transmission ports may be arranged along the circumferential direction of the RF coil or the circumferential direction of the supporting assembly. In some embodiments, the plurality of transmission ports may be distributed on at least one of the first coil portion or the third coil portion. In some embodiments, each of the plurality of transmission ports may be located on one first section of the first coil portion. In some embodiments, each of the plurality of transmission ports may be located on one second section of the second coil portion. In some embodiments, a portion of the plurality of transmission ports may be distributed on the first coil portion, and a remaining portion of the plurality of transmission ports may be distributed on the second coil portion.

In some embodiments, the coil assembly may include a plurality of electrical components supported on the supporting assembly. One of the plurality of electrical components may be operably connected to one of the plurality of transmission ports. In some embodiment, a count of the plurality of electrical components may be the same as the count of the plurality of transmission ports. The plurality of electrical components may be configured to generate the drive signal. In some embodiments, the plurality of electrical components may be arranged along the circumferential direction of the RF coil or the circumferential direction of the supporting assembly. In some embodiments, at least one of the plurality of electrical components may be located along a same circumference. For example, all of the plurality of electrical components may be located along a same circumference. In some embodiments, at least one of the plurality of electrical components may be spaced evenly. For example, all of the plurality of electrical components may be spaced evenly. In some embodiments, the at least one of the plurality of electrical components may be spaced evenly along the circumferential direction of the RF coil or the circumferential direction of the supporting assembly. It should be noted that whether the plurality of electrical components is located along a same circumference may not affect the distribution of the aggregated magnetic field generated by the RF coil. In some embodiments, the at least one of the plurality of electrical components may be spaced along an axial direction of the supporting assembly.

In some embodiments, one of the plurality of electrical components may include a cable and a cable trap. A first end of the cable may be operably connected to one of the plurality of transmission ports corresponding to the electrical component for transmitting the drive signal. In some embodiments, the transmission port may be located on one of the plurality of first sections of the first coil portion or one of the plurality of second sections of the second coil portion; that is, the first end of the cable may be operably connected to the first section or the second section. In some embodiments, the cable trap may be configured to define a frequency (e.g., 128 MHz) of the drive signal. A plurality of frequencies of a plurality of drive signals corresponding to the plurality of coil units may be the same by controlling a plurality of cable traps corresponding to the plurality of coil units. Therefore, a plurality of frequencies of the plurality of magnetic fields generated by the plurality of coil units may be the same, achieving a uniform distribution of the aggregated magnetic field ($B_1$) generated by the RF coil. In some embodiments, the supporting assembly may include at least one recess. The at least one recess may be configured to accommodate at least a portion of the plurality of cable traps.

In some embodiments, a second end of the cable may lead to a second transmission port. The second end of the cable may be different from the first end of the cable. The second transmission port may be configured to transmit a power to the cable. In some embodiments, at least some of a plurality of second transmission ports corresponding to the plurality of electrical components may be aggregated in a cable group. For example, all of the plurality of second transmission ports may be aggregated in one cable group. In some embodiments, the cable group may be located on an end of the supporting assembly along the axial direction of the supporting assembly. As another example, the plurality of second transmission ports may be aggregated in two or more cable groups. In some embodiments, second transmission ports inside one cable group may be grounded together and operably connected to a same switch component, thereby avoiding a signal phase deviation between the second transmission ports of the cable group caused by, e.g., different lengths of the second transmission ports and suppressing a common-mode signal.

In some embodiments, the supporting assembly may include at least one wiring groove. The at least one wiring groove may be configured to accommodate a plurality of cables corresponding to the plurality of electrical components. In some embodiments, at least one of the plurality of cables may be accommodated inside one of the at least one wiring groove. For example, each of the at least one wiring groove may be configured to accommodate a single cable of the plurality of cables. A count of the at least one wiring groove may be equal to or smaller than a count of the plurality of cables. In some embodiments, the at least one wiring groove may be arranged in a same portion of the supporting assembly. For example, the at least one wiring groove may be arranged in a left portion (e.g., along the negative direction of the Z-axis) of the supporting assembly. As another example, the at least one wiring groove may be arranged in a right portion (e.g., along the positive direction of the Z-axis) of the supporting assembly. By setting the at least one wiring groove, the plurality of cables may be arranged properly, avoiding the winding of the plurality of cables.

In some embodiments, the coil assembly may include a second electrical component configured for power supply (e.g., direct current (DC) power supply) of the RF coil. The second electrical component may include a second cable operably connected to the RF coil. The second cable may be configured to transmit a signal (e.g., a DC signal) as the power supply to the RF coil. In some embodiments, a first end of the second cable may be operably connected to the RF coil. A second end of the second cable and the second end of the cable may be on opposite ends along the axial direction of the supporting assembly, avoiding or reducing an interference between the RF signal and the DC signal. In some embodiments, the second end of the second cable may be different from the first end of the second cable.

In some embodiments, a direction of an electric current flowing through each coil unit may be the same or different, depending on, e.g., an amplitude and a phase of the electric current supplied to the coil unit. In some embodiments, the electric current of the coil unit may be discrete and determined according to Equation (1) below:

$$J(n) = J_0 \cos\left(\frac{2\pi n}{N}\right), \quad (1)$$

where J refers to an electric current flowing through an nth coil unit, N refers to the count of the plurality of coil units, and $J_0$ refers to a maximum electric current flowing through the N coil units. For example, assuming that N is 12 indicating that the coil assembly includes 12 coil units, and the first coil unit to the 12th coil unit are arranged in a clockwise direction, the first coil unit and the $6^{th}$ coil unit may have the maximum electric current. In some embodiments, different electric current signals may be provided to different coil units, such that amplitudes and phases of the electric currents supplied to the plurality of coil units may be the same, and a plurality of frequencies of a plurality of drive signals corresponding to the plurality of coil units may be the same. In some embodiments, an amplitude and a phase of a drive signal corresponding to one of the plurality of coil units may be adjusted by a power amplifier. Accordingly, different transmission ports may be operably connected to different power amplifiers, such that the plurality of frequencies of the plurality of coil units may be the same. The amplitude and/or the phase of the drive signal generated by each power amplifier may be set independently; that is, the amplitude and/or the phase of the drive signal of each coil unit may be set independently.

In some embodiments, the coil assembly may include at least one tuning component located along the circumferential direction of the supporting assembly. The at least one tuning component may be configured to adjust a resonance frequency of the RF coil. The at least one tuning component may include at least one adjustment portion. The at least one adjustment portion of the at least one tuning component may be located on a first end of the supporting assembly along the axial direction of the supporting assembly. An adjustment portion of a tuning component may refer to a portion of the tuning component where an adjustment to the tuning component may be made, e.g., by an operator or one or more other mechanisms, so as to adjust the resonance frequency of the RF coil.

In some embodiments, the coil assembly may include at least one coupling component located along the circumferential direction of the supporting assembly. The at least one coupling component may be configured to adjust a degree of coupling (or referred to as a coupling degree) between the plurality of coil units. The at least one tuning component may include at least one second adjustment portion. The at least one second adjustment portion of the at least one coupling component may be located on a second end of the supporting assembly along the axial direction of the supporting assembly. A second adjustment portion of a coupling component may refer to a portion of the coupling component where an adjustment to the coupling component may be made, e.g., by an operator or one or more other mechanisms, so as to adjust the coupling degree between the plurality of coil units.

In some embodiments, the first end of the supporting assembly and the second end of the supporting assembly may be the same. For example, the first end and the second end may be located in a left portion of the supporting assembly (e.g., along the negative direction of the Z-axis). As another example, the first end and the second end may be located in a right portion of the supporting assembly (e.g., along the negative direction of the Z-axis). By setting the adjustment portion(s) of the coupling component(s) and the second adjustment portion(s) of the coupling component(s) on a same side of the supporting assembly, the tuning operation and/or the coupling operation may be easily performed by, the operator or one or more other mechanisms set on a same side of the supporting assembly. In some embodiments, the first end of the supporting assembly and the second end of the supporting assembly may be different. For example, the first end and the second end of the supporting assembly may be located in a left portion and a right portion of the supporting assembly, respectively.

Figure 12:
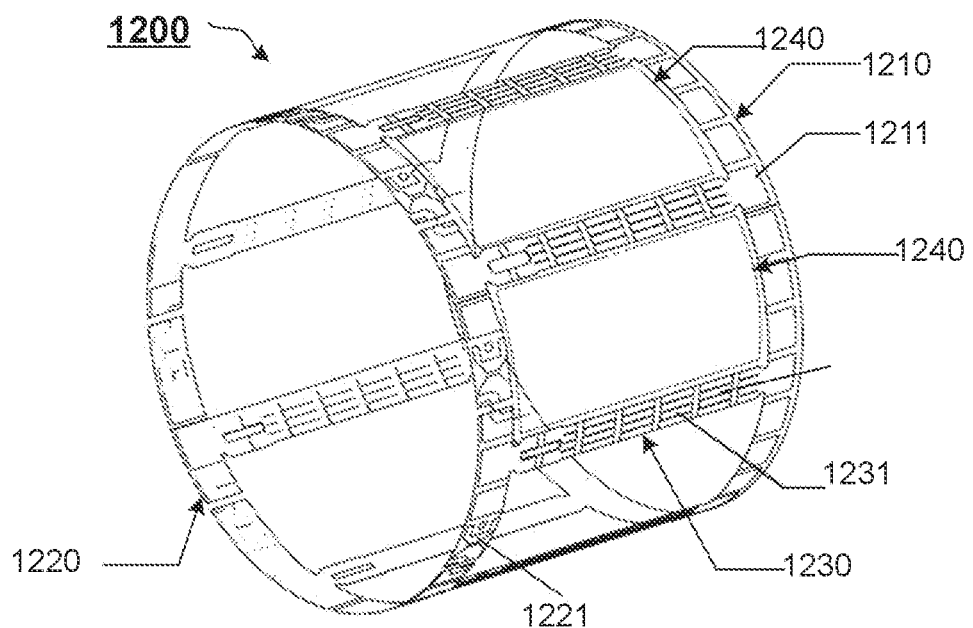
FIG. 12 is a schematic diagram illustrating an exemplary RF coil according to some embodiments of the present disclosure.
Figure 13:
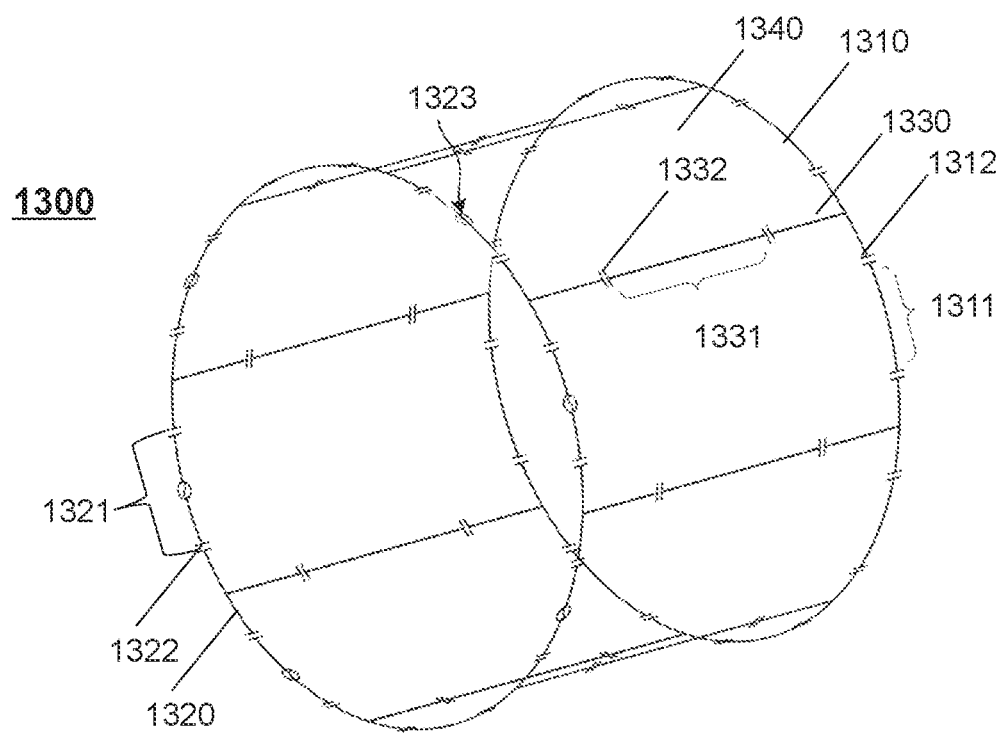
FIG. 13 is a schematic diagram illustrating an exemplary RF coil according to some embodiments of the present disclosure.

In some embodiments, the first coil portion may be divided into a plurality of first units (e.g., first units 1211 in FIG. 12 or first units 1311 in FIG. 13). Two adjacent first units of the first coil portion may be operably connected by at least one first capacitor. A first capacitor may include a fixed capacitor or an adjustable capacitor. The fixed capacitor may have a fixed capacitance. The adjustable capacitor may have an adjustable capacitance. In some embodiments, the second coil portion may be divided into a plurality of second units (e.g., second units 1221 in FIG. 12 or first units 1321 in FIG. 13). Two adjacent second units may be operably connected by at least one second capacitor. A second capacitor may include a fixed capacitor or an adjustable capacitor.

In some embodiments, each of the plurality of third coil portions may be divided into a plurality of third units (e.g., third units 1231 in FIG. 12 or first units 1331 in FIG. 13). Two adjacent third units may be operably connected by at least one third capacitor. As used herein, two units (e.g., two first units, two second units, two third units, etc., as described herein) are considered adjacent if there is no other unit of the same type and/or structure positioned between the two units. A third capacitor may include a fixed capacitor or an adjustable capacitor. For example, two adjacent third units in a middle portion of the third coil portion may be operably connected by at least one fixed capacitor, and two adjacent third units in an end portion (e.g., a left portion on the negative Z-axis, a right portion on the positive Z-axis) of the third coil portion may be operably connected by at least one adjustable capacitor. As used herein, the middle portion of the third coil portion may be located between the left portion and the right portion of the third coil portion along a long axis (e.g., the Z-axis) of the third coil portion. In some embodiments, a frequency of a drive signal corresponding to one of the plurality of coil units may be adjusted by adjusting the capacitance of at least one adjustable capacitor located in the coil unit. In some embodiments, a capacitance of one of the at least one adjustable capacitor may also be adjusted based on a positional deviation between an ideal position and an actual position of the coil unit, a difference between an ideal capacitance and an actual capacitance of the adjustable capacitor, etc. As used herein, an ideal position of a coil unit refers to a position where the coil unit is designed to be. As used herein, an ideal capacitance of a coil unit refers to a capacitance of the coil unit that is designed to have.

In some embodiments, a tuning component may include a tuning rod and a tuning capacitor. The tuning capacitor may be located on a portion (e.g., a third coil portion) of the RF coil. In some embodiments, the tuning capacitor may be operably connected to the third coil portion. In some embodiments, the tuning capacitor may be fixedly connected to the third coil portion. For example, the tuning capacitor may be welded on the third coil portion. In some embodiments, the tuning capacitor may be used as an adjustable capacitor as described elsewhere in the present disclosure. For example, two adjacent third units in the end portion of the third coil portion may be connected by the tuning capacitor. As another example, a third unit in the end portion of the third coil portion and a first unit of the first coil portion may be connected by the tuning capacitor. As a further example, a third unit in the end portion of the third coil portion and a second unit of the second coil portion may be connected by the tuning capacitor In some embodiments, at least some tuning capacitors corresponding to the at least one tuning component may be located on a same side of the axial direction of the supporting assembly. The tuning rod of the tuning component may extend axially along the supporting assembly. The tuning rod may be rotatably connected to the tuning capacitor. The tuning rod may be configured to rotate axially for adjusting a capacitance of the tuning capacitor. In some embodiments, the tuning capacitor may include metal pieces. At least some of the metal pieces may oppose each other. A distance between the metal pieces inside the tuning capacitor or a surface area between the metal pieces in an opposing configuration may be adjusted by rotating the tuning rod, thereby adjusting the capacitance of the tuning capacitor.

In some embodiments, a coupling component may include a coupling rod and a coupling capacitor. The coupling capacitor may be located on the first coil portion or the second coil portion. The coupling capacitor may be configured to connect at least some adjacent first units of the first coil portion or at least some adjacent second units of the second coil portion. The coupling capacitor may be used as an adjustable capacitor as described elsewhere in the present disclosure. Taking three adjacent first (or second) units as an example, two adjacent first (or second) units may be connected by the fixed capacitor, and another two adjacent first (or second) units may be connected by the coupling capacitor. In some embodiments, the coupling rod of the coupling component may extend axially along with the supporting assembly. The coupling rod may be rotatably connected to the coupling capacitor. The coupling rod may be configured to rotate axially for adjusting a coupling degree between the at least some adjacent first (or second) units. In some embodiments, the coupling capacitor may include metal pieces. At least some of the metal pieces may oppose each other. A distance between the metal pieces inside the coupling capacitor or a surface area between the metal pieces in an opposing configuration may be adjusted by rotating the coupling rod, thereby adjusting a resistance of the coupling capacitor, achieving the decoupling between the at least some adjacent first (or second) units and avoiding the damage of the RF coil caused by the coupling. In some embodiments, the structure and/or the principle of operation of the coupling component may be the same as or similar to the structure and/or the principle of operation of the tuning component, the descriptions of which are not repeated.

In some embodiments, a tuning component may further include a tuning sleeve. The tuning sleeve may be located on the tuning rod of the tuning component. There may be a gap between the tuning sleeve and the tuning capacitor of the tuning component for exposing at least a portion of the tuning rod. An exposed portion of at least one tuning rod of the tuning component may be located on the first end of the supporting assembly along the axial direction of the supporting assembly. In some embodiments, the capacitance of the tuning capacitor may be adjusted by adjusting the exposed portion, for example, using a screwdriver.

In some embodiments, a coupling component may further include a coupling sleeve. The coupling sleeve may be located on the coupling rod of the tuning component. There may be a gap between the coupling sleeve and the coupling capacitor of the coupling component for exposing at least a portion of the coupling rod. An exposed portion of at least one coupling rod corresponding to the at least one coupling component may be located on the second end of the supporting assembly along the axial direction of the supporting assembly. In some embodiments, the capacitance of the coupling capacitor may be adjusted by adjusting the exposed portion, for example, using a screwdriver.

Figure 10:
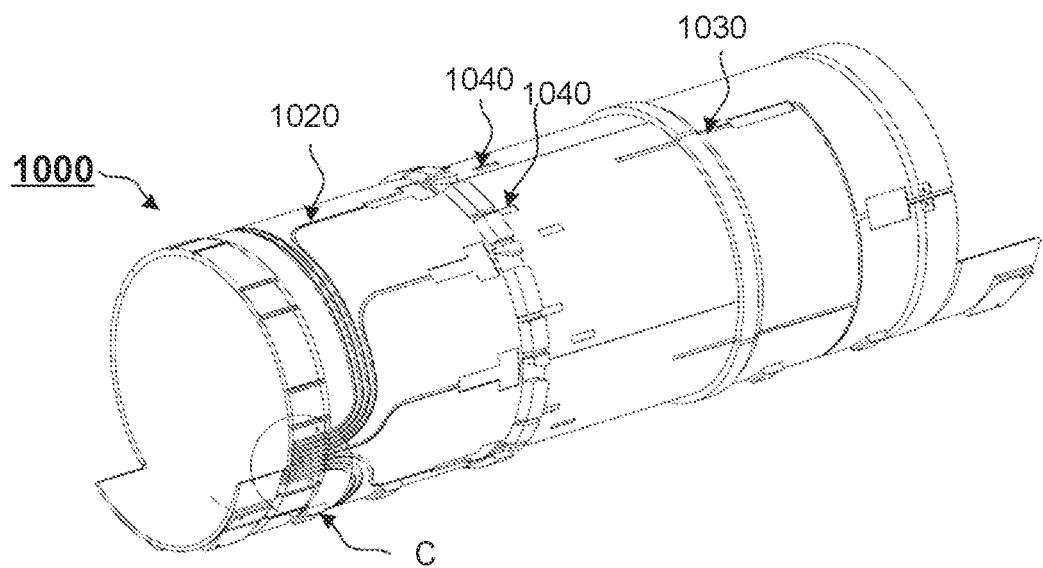
FIG. 10 is a schematic diagram illustrating an exemplary supporting assembly according to some embodiments of the present disclosure.

In some embodiments, the supporting assembly may include at least one recess (e.g., recesses 1040 in FIG. 10). The at least one recess may be configured to accommodate at least one of the at least one tuning capacitor or the at least one coupling capacitor. In some embodiments, the at least one recess may extend inwardly along a radial direction of the supporting assembly. Accordingly, the at least one tuning capacitor and/or the at least one coupling capacitor may sink inside the supporting assembly, simplifying the space design of the coil assembly. In some embodiments, there may be a gap between the supporting assembly and the tuning capacitor (or the coupling capacitor); that is, the tuning capacitor (or the coupling capacitor) suspends in but is not in contact with the recess. Such an arrangement may avoid or reduce overheating the wall of the supporting assembly caused by heat generated by the tuning capacitor and/or the coupling capacitor during an operation of the coil assembly.

Figure 6:
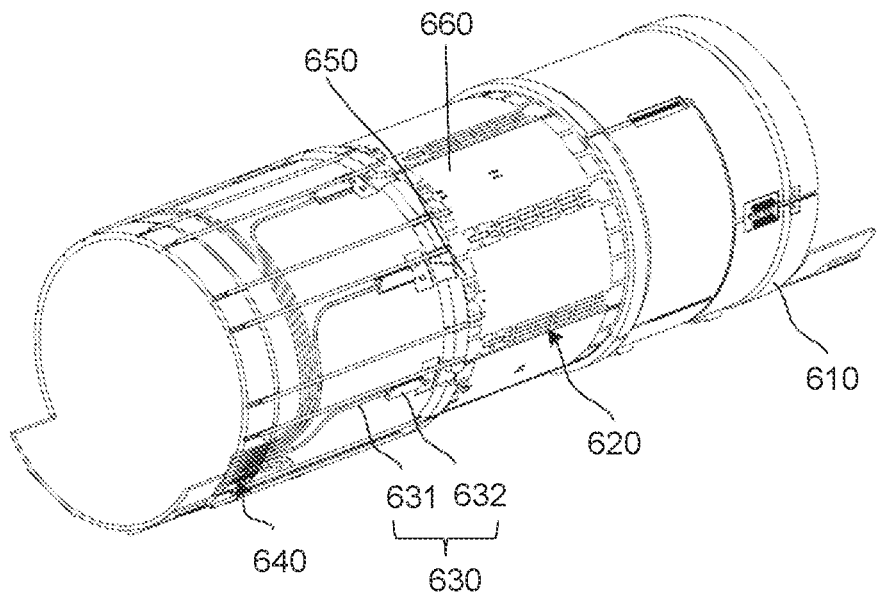
FIG. 6 is a schematic diagram illustrating an exemplary coil assembly according to some embodiments of the present disclosure.

FIG. 6 is a schematic diagram illustrating an exemplary coil assembly according to some embodiments of the present disclosure.

As shown in FIG. 6, the coil assembly 600 may include a supporting assembly 610 (e.g., a hollow cylinder) and an RF coil 620. The RF coil 620 may be supported on the supporting assembly 610. The RF coil 620 may include a plurality of coil units 660 and a plurality of transmission ports 650. In some embodiments, each of the plurality of transmission ports 650 may be connected to a single coil unit of the plurality of coil units 660.

As shown in FIG. 6, the coil assembly 600 may include a plurality of electrical components 630 supported on the supporting assembly 610. Each of the plurality of electrical components 630 may be connected to a single transmission port of the plurality of transmission ports 650. The electrical component 630 may include a cable 631 and a cable trap 632. Cables corresponding to the plurality of electrical components 630 may be aggregated in a cable group 640.

Figure 7:
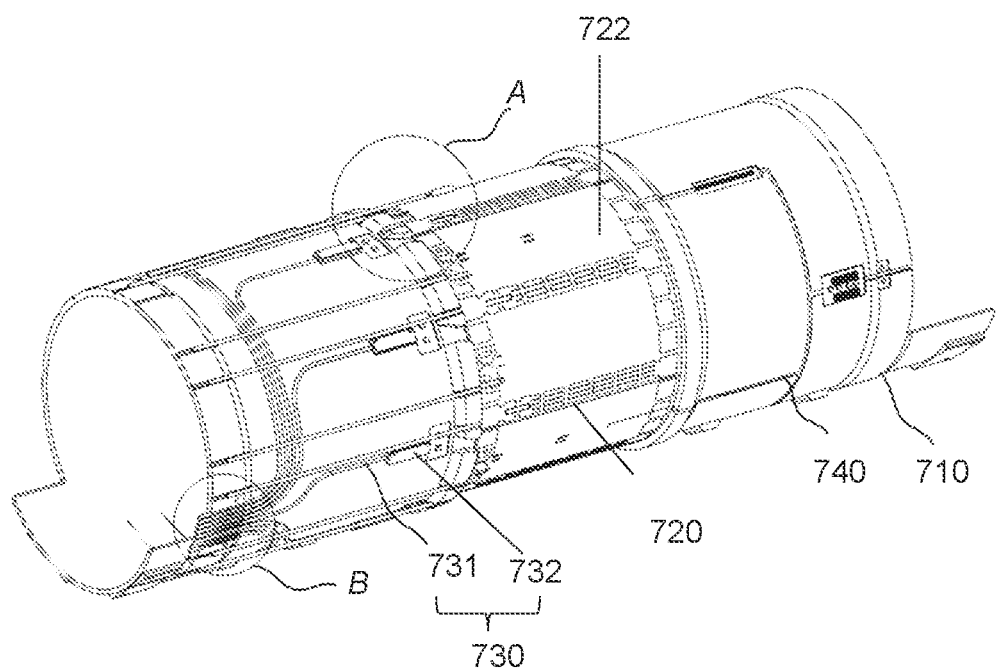
FIG. 7 is a schematic diagram illustrating an exemplary coil assembly according to some embodiments of the present disclosure.

FIG. 7 is a schematic diagram illustrating an exemplary coil assembly according to some embodiments of the present disclosure.

As shown in FIG. 7, the coil assembly 700 may include a supporting assembly 710 (e.g., a hollow cylinder) and an RF coil 720. The RF coil 720 may be supported on the supporting assembly 710. The RF coil 720 may include a plurality of coil units 722. The coil assembly 700 may also include a plurality of electrical components 730. The plurality of electrical components 730 may be configured to generate drive signals used to generate a plurality of magnetic fields by the plurality of coil units 722, respectively. The electrical component 730 may include a cable 731 and a cable trap 732. Cables corresponding to the plurality of electrical components 730 may be aggregated at a portion B of the supporting assembly 710. The coil assembly 700 may include a second electrical component for power supply of the coil assembly 700. The second electrical component may include a second cable 740. The second cable 740 and the cable 731 may be on opposite ends along an axial direction of the supporting assembly 710.

Figure 8:
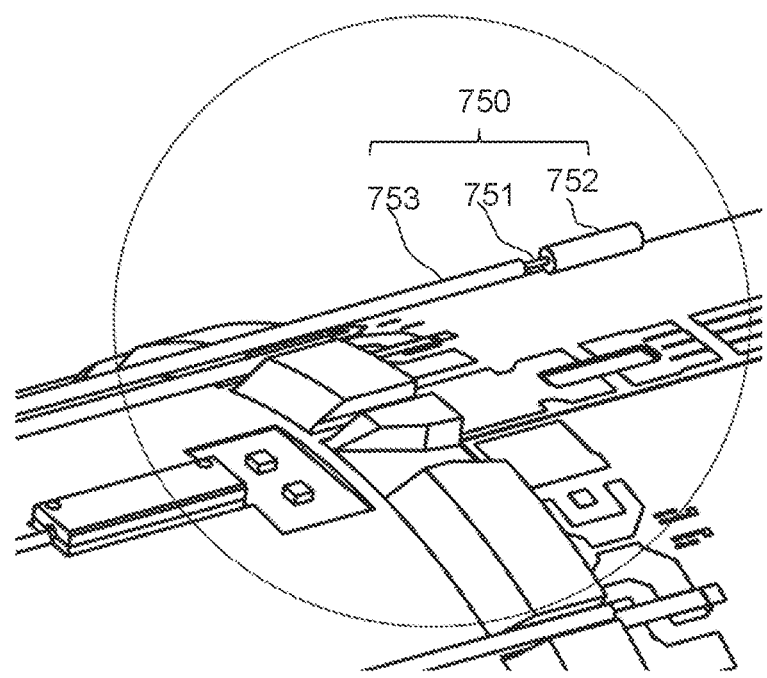
FIG. 8 is an enlarged view illustrating portion A of the coil assembly in FIG. 7 according to some embodiments of the present disclosure.
Figure 9:
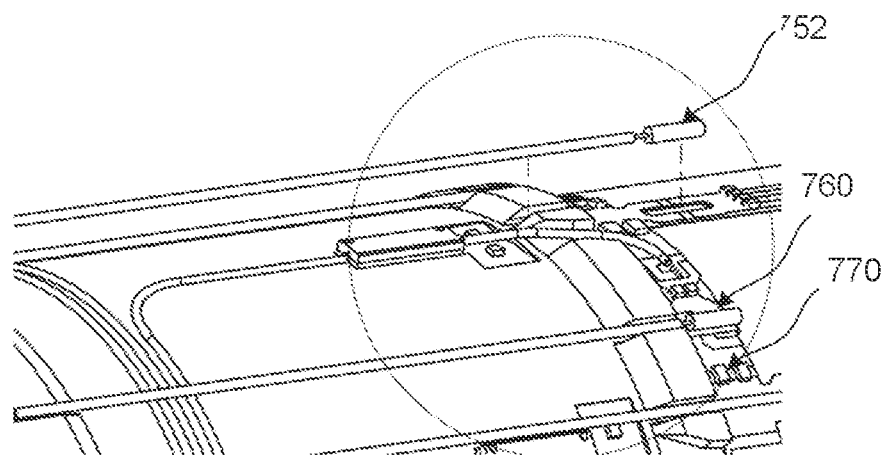
FIG. 9 is an enlarged view illustrating portion A of the coil assembly in FIG. 7 according to some embodiments of the present disclosure.

FIG. 8 is an enlarged view illustrating portion A of the coil assembly 700 in FIG. 7 according to some embodiments of the present disclosure. FIG. 9 is an enlarged view illustrating portion A of the coil assembly 700 in FIG. 7 according to some embodiments of the present disclosure.

As shown in FIG. 8, the coil assembly 700 may include a tuning component 750 supported on the supporting assembly 710. The tuning component 750 may be configured to adjust a resonance frequency of the RF coil 720. The tuning component 750 may include a tuning rod 751, a tuning capacitor 752, and a tuning sleeve 753. The tuning rod 751 may be rotatably connected to the tuning capacitor 752. The tuning rod 751 may be configured to rotate axially for adjusting a capacitance of the tuning capacitor 752. The tuning sleeve 753 may be located on the tuning rod 751. There may be a gap between the tuning sleeve 753 and the tuning capacitor 752 for exposing a portion of the tuning rod 751. The capacitance of the tuning capacitor 752 may be adjusted by adjusting the exposed portion, for example, using a screwdriver.

As shown in FIG. 9, the coil assembly 700 may also include a coupling capacitor 760 and a fixed capacitor 770. In some embodiments, the coupling capacitor 760 may have an adjustable capacitance. The coupling capacitor 760 may be configured to adjust a coupling degree between at least a portion of the plurality of coil units 722. In some embodiments, the fixed capacitor 770 may have a fixed capacitance.

Figure 11:
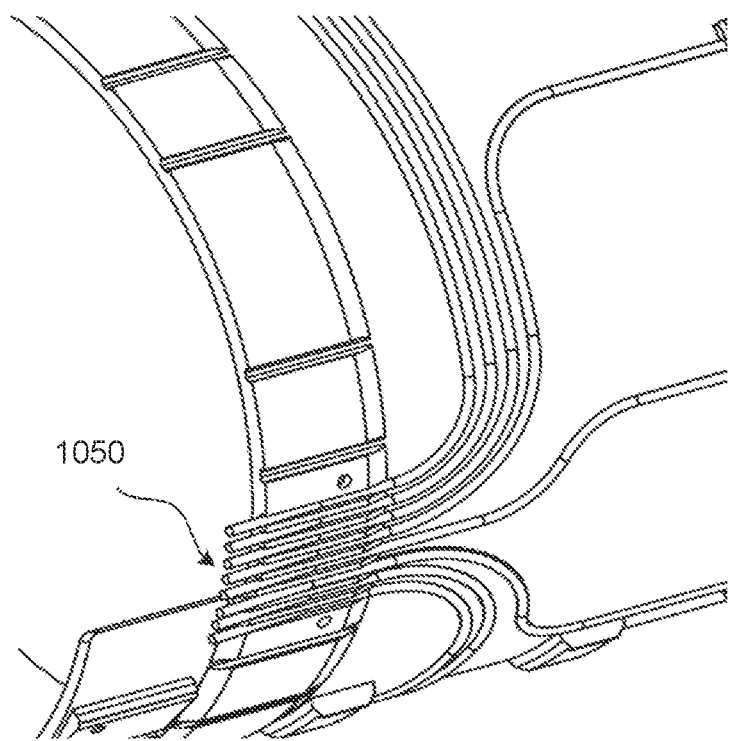
FIG. 11 is an enlarged view illustrating portion C of the supporting assembly in FIG. 10 according to some embodiments of the present disclosure.

FIG. 10 is a schematic diagram illustrating an exemplary supporting assembly according to some embodiments of the present disclosure. FIG. 11 is an enlarged view illustrating portion C of the exemplary supporting assembly according to some embodiments of the present disclosure.

As shown in FIG. 10, a plurality of first wiring grooves 1020 may be supported on the supporting assembly 1000. The plurality of first wiring grooves 1020 may be configured to accommodate a plurality of second transmission ports, respectively, and aggregate a portion of each of the plurality of second transmission ports at a portion of the supporting assembly 1000 (e.g., portion C). The portion of each of the plurality of second transmission ports may be aggregated in a cable group 1050. The plurality of second transmission ports may be configured to transmit powers to a plurality of cables of a plurality of electrical components, respectively. The plurality of electrical components may be configured to generate drive signals used to generate a plurality of magnetic fields by a plurality of coil units of an RF coil, respectively. The RF coil may be supported on the supporting assembly 1000.

As shown in FIG. 10, a second wiring groove 1030 may also be supported on the supporting assembly 1000. The second wiring groove 1030 may be configured to accommodate a second cable of a second electrical component. The second electrical component may be configured for power supply of the RF coil. The plurality of first wiring grooves 1020 and the second wiring groove 1030 may be located on opposite ends along an axial direction of the supporting assembly 1000.

FIG. 12 is a schematic diagram illustrating an exemplary RF coil according to some embodiments of the present disclosure.

As shown in FIG. 12, the RF coil 1200 may include a first coil portion 1210, a second coil portion 1220, and a plurality of third coil portions 1230, forming a plurality of coil units 1240. The first coil portion 1210 and the second coil portion 1220 may be located at an end of each of the plurality of third coil portions 1230, respectively; that is, the plurality of third coil portions 1230 may be located between the first coil portion 1210 and the second coil portion 1220. The third coil portion 1230 may be connected to a position of the first coil portion 1210 and a position of the second coil portion 1220, respectively. Accordingly, the plurality of third coil portions 1230 may divide the first coil portion 1210 into a plurality of first sections and divide the second coil portion into a plurality of second sections. A first section between two adjacent third coil portions 123 and a second section between the two adjacent third coil portions 123, in combination with the two adjacent third coil portions 1230, may form one of the plurality of coil units 1240.

FIG. 13 is a schematic diagram illustrating an exemplary RF coil according to some embodiments of the present disclosure.

As shown in FIG. 13, the RF coil 1300 may include a first coil portion 1310, a second coil portion 1320, and a plurality of third coil portions 1330, forming a plurality of coil units 1340. The first coil portion 1310 may include a plurality of first units 1311, two adjacent of which are connected by at least one capacitor 1312. The second coil portion 1320 may include a plurality of second units 1321, two adjacent of which are connected by at least one capacitor 1322. Each of the plurality of third coil portions 1330 may include a plurality of third units 1331, two adjacent of which are connected by at least one capacitor 1332. The RF coil 1300 may also include a plurality of transmission ports 1323. Each of the plurality of transmission ports 1323 may be located on one of the plurality of second units 1321. The plurality of transmission ports 1323 may be configured to transmit drive signals to the plurality of coil units 1340 for generating magnetic fields, respectively.

Figure 14:
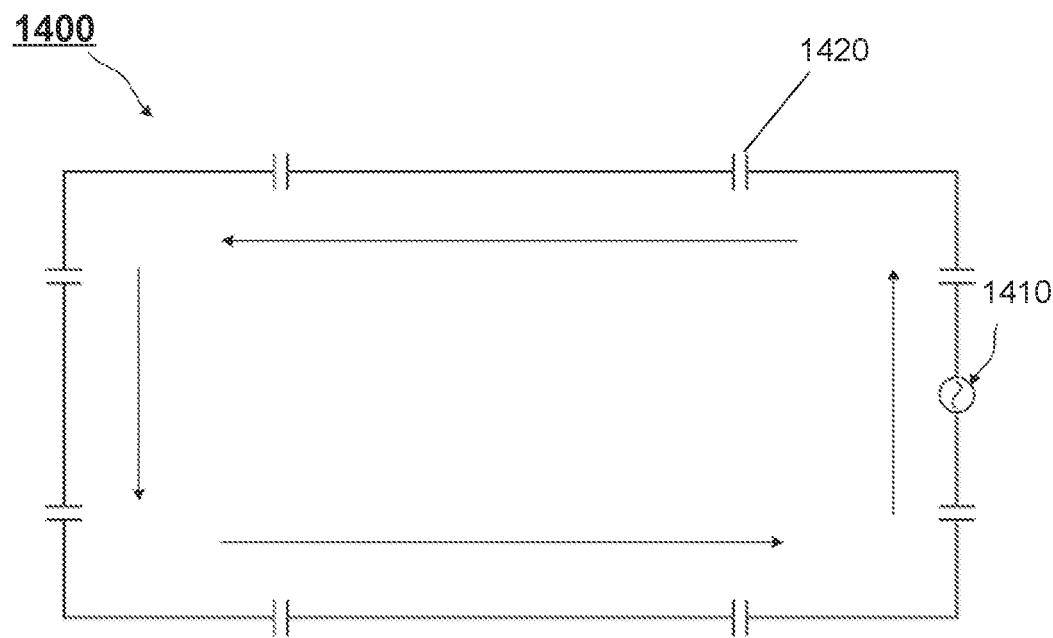
FIG. 14 is a schematic diagram illustrating an exemplary coil unit according to some embodiments of the present disclosure.

FIG. 14 is a schematic diagram illustrating an exemplary coil unit according to some embodiments of the present disclosure. As shown in FIG. 14, the coil unit 1400 may include a transmission port 1410 and a plurality of capacitors 1420. The transmission port 1410 may be configured to transmit a drive signal to the coil unit 1400 for generating a magnetic field.

Figure 15:
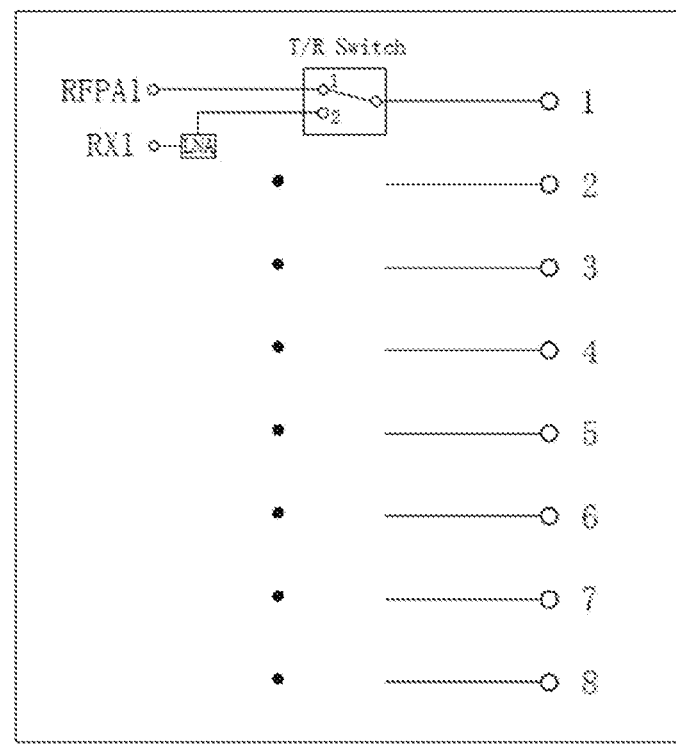
FIG. 15 is a schematic diagram illustrating an exemplary switch unit of a switch component according to some embodiments of the present disclosure.

FIG. 15 is a schematic diagram illustrating an exemplary switch unit of a switch component according to some embodiments of the present disclosure.

In some embodiments, a coil assembly may include a plurality of transmission ports and a plurality of electrical components. The plurality of electrical components may include a plurality of cables (lines 1-8 in FIG. 15). Each of the plurality of transmission ports may be operably connected to an end of one of the plurality of cables for transmitting a drive signal for generating a magnetic field. Second ends of the plurality of cables may lead to a plurality of second transmission ports. Each of the plurality of second transmission ports may be configured to transmit a power to one of the plurality of cables.

In some embodiments, the plurality of second transmission ports may be aggregated in a cable group and then operably connect to a switch component. As shown in FIG. 15, the switch component 1500 may include a plurality of switch units (e.g., T/R switches). Each of the plurality of second transmission ports or the plurality of cables may be operably connected to one of the plurality of switch units. If a second transmission port is connected to an RFPA by a corresponding switch unit, an RF coil of the coil assembly may be at a transmitting status; if the second transmission port is connected to a receiving channel (RX) by the corresponding switch unit, the RF coil of the coil assembly may be at a receiving status. For example, the switch unit may include a single-pole double-throw (SPDT) switch.

According to some embodiments of the present disclosure, an MRI scanner may include at least one coil assembly. Each of the at least one coil assembly may include a supporting assembly and an RF coil. The RF coil may be supported on the supporting assembly. The RF coil may have a plurality of coil units and a plurality of transmission ports. At least one of the plurality of transmission ports may be operably connected to a single cable of the plurality of coil units. Each of the plurality of transmission ports may be configured to transmit a drive signal to one of the plurality of coil units for generating a magnetic field. The RF coil may generate an aggregated magnetic field formed by a plurality of magnetic fields each of which is generated based on one of the plurality of coil units. The structure of the coil assembly may be the same as or similar to the coil assembly illustrated below, the descriptions of which are not repeated.

According to some embodiments of the present disclosure, an MRI system may include at least one coil assembly. Each of the at least one coil assembly may include a supporting assembly and an RF coil. The RF coil may be supported on the supporting assembly. The RF coil may have a plurality of coil units and a plurality of transmission ports. At least one of the plurality of transmission ports may be operably connected to a single coil unit of the plurality of coil units. Each of the plurality of transmission ports may be configured to transmit a drive signal to one of the plurality of coil units for generating a magnetic field. The RF coil may generate an aggregated magnetic field formed by a plurality of magnetic fields each of which is generated based on one of the plurality of coil units. The structure of the coil assembly may be the same as or similar to the coil assembly illustrated below, the descriptions of which are not repeated.

In some embodiments, the MRI system may include a control assembly operably connected to the at least one coil assembly. The control assembly may be configured to control the generation of the magnetic field. In some embodiments, the control assembly may include a field-programmable gate array (FPGA) control unit, a digital to analog converter (DAC), an RF amplifier, and a power divider. An RF sequence transmitted by the FPGA control unit may be converted into an analog signal by the DAC, and be amplified by the RF amplifier, and be converted into the drive signal by the power divider, and further be transmitted to at least a portion (e.g., the plurality of transmission ports thereof) of the RF coil for driving the RF coil (e.g., the coil unit thereof) to generate the magnetic field (e.g., a magnetic field of circular polarization).

In some embodiments of the present disclosure, a coil assembly may include an RF coil and a plurality of dielectric components. The RF coil may be configured to generate a magnetic field ($B_1$). The magnetic field ($B_1$) may be applied to excite nuclear spins inside an object (e.g., a patient), and an image of the object may be generated based on an MR signal determined based on the nuclear spins. The object may be placed in a cavity of the coil assembly; that is, the coil assembly may surround the object, for example, by 360 degrees.

In some embodiments, the quality of an MR image may be affected by the homogeneity of the magnetic field ($B_1$). The homogeneity of the magnetic field ($B_1$) may be affected by an intensity of a main magnetic field ($B_0$). In some embodiments, the larger the intensity of the main magnetic field ($B_0$) is, the larger an operation frequency of the RF coil may be, and the lower the homogeneity of the magnetic field ($B_1$) may be. The plurality of dielectric components may be configured to adjust the homogeneity of the magnetic field ($B_1$). The plurality of dielectric components may generate an electrical field between the RF coil and the object. For example, a capacitor may form between the RF coil and the object. The electrical field may couple energy from the coil assembly to the object. An intensity of the magnetic field ($B_1$) corresponding to a region where at least one of the plurality of dielectric components is located may increase, thereby adjusting the homogeneity of the magnetic field ($B_1$).

In some embodiments, a reference distribution of a reference magnetic field ($B_1$) generated by a reference coil assembly may be predetermined. The reference coil assembly may be similar to the coil assembly except that the reference coil assembly includes no dielectric component. A remaining portion of the reference coil assembly may be the same as a corresponding portion of the coil assembly other than the plurality of dielectric components of the coil assembly. In some embodiments, the plurality of dielectric components may be placed at one or more positions where the reference intensity in the reference magnetic field ($B_1$) is relatively weak than other regions of the reference magnetic field ($B_1$), thereby improving the homogeneity of the magnetic field ($B_1$).

In some embodiments, the plurality of dielectric components may be made of a dielectric material. In some embodiments, the dielectric material may be in the form of powder, gel, sheet, etc. In some embodiments, the homogeneity of the magnetic field ($B_1$) may be adjustable by adjusting at least one parameter of the plurality of dielectric components, for example, a dielectric constant of the dielectric material, a size of one of the plurality of dielectric components, an amount of the dielectric material in the dielectric component, a type of the dielectric material, or the like, or any combination thereof. In some embodiments, the higher the dielectric constant of the dielectric material is, the higher the energy coupled from the RF coil to the object may be. The dielectric material of the dielectric component may have a relatively high dielectric constant (e.g., exceeding a threshold (e.g., 200)). For example, the dielectric material may include barium titanate, calcium titanate, magnesium titanate, titanium dioxide, or the like, or an alloy thereof.

In some embodiments, the plurality of dielectric components may be located on the RF coil. In some embodiments, the plurality of dielectric components may be located inside the RF coil. In some embodiments, the RF coil may include an antenna and a conductor (e.g., a copper sheet). For example, the plurality of dielectric components may be located between the antenna and the object. As another example, the plurality of dielectric components may be located inside the conductor. As a further example, the plurality of dielectric components may be located outside the conductor.

In some embodiments, different portions of the object may have different rates of absorption of the magnetic field ($B_1$) due to, e.g., the type(s) of tissue in the different portions of the object. In order to improve the homogeneity of the magnetic field ($B_1$) when the RF coil is used for different portions of the objects, the position and/or the at least one parameter of the plurality of dielectric components may also adjust based on the different rates of absorption of the different portions of the object. In some embodiments, the reference coil assembly may scan a reference object (e.g., a phantom) to obtain a second reference distribution of the reference magnetic field ($B_1$) after being absorbed by the object. In some embodiments, the plurality of dielectric components may be placed at one or more positions where the second reference intensity in the reference magnetic field ($B_1$) after being absorbed by the object is relatively weak than other regions of the reference magnetic field ($B_1$) after being absorbed by the object, thereby improving the homogeneity of the magnetic field ($B_1$) after being absorbed by the object.

In some embodiments, the coil assembly may include a supporting assembly configured to support the RF coil. The supporting assembly may be the same as or similar to the supporting assembly of the coil assembly illustrated above, the descriptions of which are not repeated. In some embodiments, the coil assembly may include a second supporting assembly. The second supporting assembly may be configured to support the plurality of dielectric components. In some embodiments, the second supporting assembly may be located on the RF coil. In some embodiments, the second supporting assembly may be located inside the RF coil. In some embodiments, the second supporting assembly may be located outside the RF coil. For example, the second supporting assembly may be located between the antenna and the object.

In some embodiments, the second supporting assembly may include a plurality of supporting units. Each of the plurality of supporting units may be configured to support at least one of the plurality of dielectric components. The plurality of supporting units may be spaced apart from each other or arranged side by side. In some embodiments, a shape and/or a size of the second supporting assembly may match a shape and/or a size of the RF coil. Taking the RF coil having a cylindrical shape as an example, the plurality of supporting units may be arranged along a circumferential direction of the RF coil and form the cylindrical shape; that is, the second supporting assembly may have the cylindrical shape. In some embodiments, the RF coil and the second supporting assembly may be integrated in one piece. In some embodiments, the second supporting assembly may be detachably connected to the RF coil.

In some embodiments, the second supporting assembly may include a plurality of containers, each of which forms by one of the plurality of supporting units. Similar to the plurality of supporting units, the plurality of containers may be spaced apart from each other or arranged side by side. In some embodiments, the coil assembly may include a plurality of accommodating components. The plurality of accommodating components may be designed based on the plurality of containers and/or the plurality of supporting units. At least one of the plurality of accommodating components may be located on one of at least a portion of the plurality of containers. In some embodiments, the plurality of dielectric components may be accommodated in the plurality of accommodating components. In some embodiments, one of the plurality of accommodating components may be pullable with respect to a corresponding container along an extension direction of the container (e.g. an axial direction of the supporting assembly). The second supporting assembly and the plurality of accommodating components may form a structure similar to a drawer. In some embodiments, the accommodating component may be detachably connected to the corresponding container. In some embodiments, a count of the plurality of accommodating components may be smaller than or equal to a count of the containers or a count of the supporting units. When the count of the plurality of accommodating components is smaller than the count of the containers or the count of the supporting units, the plurality of accommodating components may be located in a portion of the containers at intervals. In some embodiments, the at least one dielectric component and the accommodating component may be integrated in one piece. In some embodiments, the supporting assembly and the accommodating component may be integrated in one piece.

In some embodiments, at least a portion of the plurality of accommodating components may be employed for positioning the plurality of dielectric components based on the reference distribution of the magnetic field ($B_1$) or the second reference distribution of the magnetic field ($B_1$) after being absorbed by the object.

In some embodiments, a portion of the second supporting assembly may be located on an inner wall of the RF coil and a remaining portion of the second supporting assembly may be located inside the RF coil. There may be a space between the inner wall of the RF coil and the second supporting assembly, forming the plurality of containers. The plurality of the accommodating components may be located in the plurality of containers and located inside the RF coil. In some embodiments, the plurality of containers may face the inner wall of the RF coil. In some embodiments, the plurality of containers may face the remaining portion of the second supporting assembly.

In some embodiments, a portion of the second supporting assembly may be located on an outer wall of the RF coil and a remaining portion of the second supporting assembly may be located outside the RF coil. There may be a space between the outer wall of the RF coil and the second supporting assembly, forming the plurality of containers. The plurality of the accommodating components may be located in the plurality of containers and located outside the RF coil. In some embodiments, the remating portion of the second supporting assembly may be located between the outer wall of the RF coil and a gradient coil of the coil assembly.

In some embodiments, a distance between the supporting assembly and the object may be adjustable, thereby adjusting a distance between the plurality of dielectric components and the object and/or adjusting space between the supporting assembly and the object. For example, the distance between the supporting assembly and a thin object may be smaller than the distance between the supporting assembly and a fat object.

In some embodiments, one of the plurality of supporting units may include a supporting base (e.g., a plate) and at least one baffle located at least one side of the supporting base. For example, the at least one baffle may include two baffles located at two sides of the supporting base. The supporting base and the at least one baffle may form the supporting unit, and a corresponding accommodating component is supported on the supporting unit. The at least one baffle may be configured to limit movement of the corresponding accommodating component. After an end of the corresponding accommodating component is located on a first end of the supporting base, at least one edge of the corresponding accommodating component may contact the at least one baffle, and the at least one baffle may guide movement of the corresponding accommodating component inside a corresponding container, avoiding the corresponding accommodating component deviating from the corresponding container and ensuring accurate match between the corresponding accommodating component and the supporting unit.

In some embodiments, one of the plurality of supporting units (e.g., the at least one baffle thereof) and the corresponding accommodating component may include a groove, and another one of the supporting unit and the corresponding accommodating component may include a protrusion. The corresponding accommodating component may slide along the supporting unit by matching the groove and the protrusion, ensuring the accuracy of a movement trajectory of the corresponding accommodating component. In some embodiments, the supporting base and the at least one baffle may be integrated in one piece.

In some embodiments, the supporting unit may include a limiting piece (e.g., a pillar). The limiting piece may be located at a second end of the supporting unit. The second end of the supporting unit may be different from the first end of the supporting unit. The first end of the supporting unit and the second end of the supporting unit may be on opposite ends along an axial direction of the supporting unit. The limiting piece may be configured to limit a position of the corresponding accommodating component. When the corresponding accommodating component is supported on the supporting unit and moves to the corresponding container, the corresponding accommodating component may stop moving in response to contacting the limiting piece. Therefore, a position of at least one dielectric component in the corresponding accommodating component may be controlled accurately.

In some embodiments, the supporting unit may be connected to the RF coil through the at least one baffle in various connection manners. For example, the connection manners may include an adhesive manner (e.g., a heat-activated adhesive manner, a co-adhesive manner, a tape manner (e.g., a pressure-sensitive tape manner, a glue manner)), a welding manner, a buckling manner, a screwing manner, or the like, or any combination thereof.

In some embodiments, one of the plurality of accommodating components may include an accommodating base (e.g., a plate) and at least one second limiting piece (e.g., at least one plate). The at least one second limiting piece may surround the accommodating component. The accommodating base and the at least one second limiting piece may form a cavity, and the cavity may be used to accommodate at least one of the plurality of dielectric components. For example, the at least one limiting piece may surround four sides of the accommodating component and form a cavity with the top opening.

After a portion of the accommodating component is supported on the supporting unit, the at least one second limiting piece may contact the at least one baffle, and a remaining portion of the accommodating component may mount on the supporting unit by matching the at least one second limiting piece and the at least one baffle, avoiding the movement of the accommodating component towards the at least one baffle. In some embodiments, the at least one second limiting piece may limit the movement of the at least one dielectric component, thereby accurately controlling a position of the at least one dielectric component in the accommodating component.

In some embodiments, the accommodating component may include at least one separating piece inside the cavity. The at least one separating piece may be configured to separate the cavity into a plurality of sub-cavities. Different dielectric components may be located in different sub-cavities. In some embodiments, at least one parameter of at least one dielectric component in each cavity or each sub-cavity may be the same or different, for example, a dielectric constant of a dielectric material of the at least one dielectric component, a size of the at least one dielectric component, an amount of the dielectric material in the at least one dielectric component, a type of the dielectric material, or the like, or any combination thereof.

It should be noted that the above descriptions are non-limiting. In some embodiments, if openings of the plurality of containers face the RF coil, the supporting assembly may be unnecessary, the plurality of dielectric components may be supported by the RF coil.

According to some embodiments of the present disclosure, a coil assembly may include an RF coil and a second supporting assembly. The second supporting assembly may be fixed or flexibly connected to the RF coil. The second supporting assembly may include a plurality of containers. The plurality of containers may extend along an axial direction of the second supporting assembly. At least one opening for arranging the plurality of containers may be located on a first end surface and/or a second end surface of the supporting assembly. The RF coil may be configured to emit an RF signal. The RF signal may be applied to excite nuclear spins inside of an imaging region of an object to generate an MR signal. The MR signal may be used to determine imaging information of the imaging region. The coil assembly may also include a plurality of dielectric components. The second supporting assembly may be configured to support the plurality of dielectric components. The plurality of dielectric components may be configured to adjust a distribution of a magnetic field generated by the RF coil and improve homogeneity of the magnetic field, thereby improving the accuracy of the imaging information of the imaging region.

In some embodiments, the coil assembly may include a plurality of accommodating components. The plurality of accommodating components may be located in the plurality of containers, respectively. In some embodiments, each of at least a portion of the plurality of accommodating components may have at least one separating piece. The at least one separating piece may divide the accommodating component into a plurality of sub-cavities. It should be noted that the above descriptions are non-limiting. In some embodiments, if openings of the plurality of containers face the RF coil, the supporting assembly may be unnecessary, the plurality of dielectric components may be supported by the RF coil.

In some embodiments, the second supporting assembly may be located inside the RF coil. In some embodiments, the second supporting assembly may be located outside the RF coil. For example, the second supporting assembly may be located between the RF coil and a gradient coil of the coil assembly. In some embodiments, the second supporting assembly may be retractable, e.g., along a radial direction of the RF coil. More descriptions of the coil assembly may be found in the descriptions of the coil assembly.

According to some embodiments of the present disclosure, an MRI scanner may include a patient support and a coil assembly. The coil assembly may be located in a bore of the MRI scanner. The patient support may be configured to support an object and move the object inside or outside of the bore of the MRI scanner for imaging. In some embodiments, the coil assembly may include an RF coil and a plurality of dielectric components. The RF coil may be configured to generate a magnetic field ($B_1$). The magnetic field ($B_1$) may be applied to excite nuclear spins inside the object, and an image of the object may be generated based on an MR signal determined based on the nuclear spins. The plurality of dielectric components may be located inside or outside the RF coil. In some embodiments, the coil assembly may also include a plurality of accommodating components configured to accommodate the plurality of dielectric components, respectively.

In some embodiments, the coil assembly may include a second supporting assembly. The second supporting assembly may be located on the RF coil. The second supporting assembly may include a plurality of containers arranged side by side or spaced each other. The plurality of accommodating components may be located in the plurality of containers, for example, through a pullable manner. In some embodiments, the coil assembly may be the same as or similar to the coil assembly or the coil assembly illustrated above, the descriptions of which are not repeated.

Figure 16:
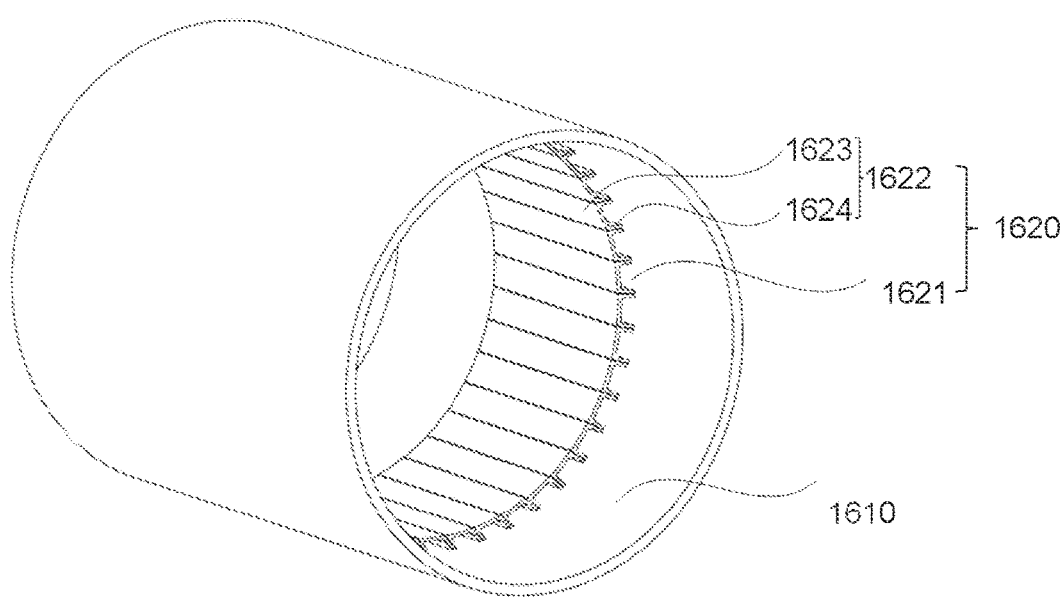
FIG. 16 is a schematic diagram illustrating an exemplary coil assembly according to some embodiments of the present disclosure.

FIG. 16 is a schematic diagram illustrating an exemplary coil assembly according to some embodiments of the present disclosure. The coil assembly 1600 may be an example of the coil assembly described elsewhere in the present disclosure.

As shown in FIG. 16, the coil assembly 1600 may include an RF coil 1610 and a second supporting assembly 1620. The second supporting assembly 1620 may include a plurality of supporting units 1622 arranged along a circumferential direction of the RF coil 1610. The second supporting assembly 1620 may also include a plurality of containers 1621 formed by the plurality of supporting units, respectively. The plurality of containers 1621 may be arranged along the circumferential direction of the RF coil 1610. A supporting unit 1622 may include a supporting base 1623 and two baffles 1624, forming one of the plurality of containers 1621. The two baffles 1624 may be located on two sides of the supporting base 1623.

Figure 17:
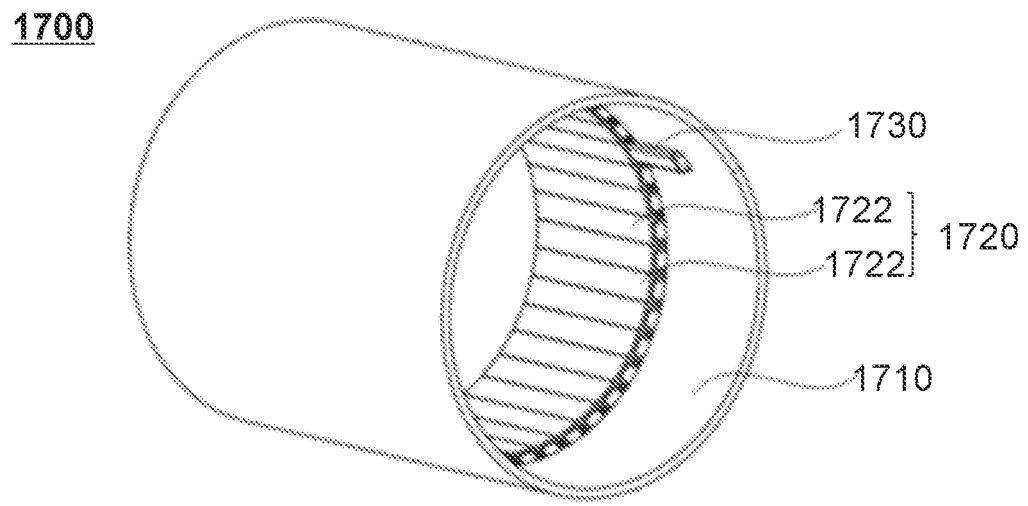
FIG. 17 is a schematic diagram illustrating an exemplary coil assembly according to some embodiments of the present disclosure.
Figure 18:
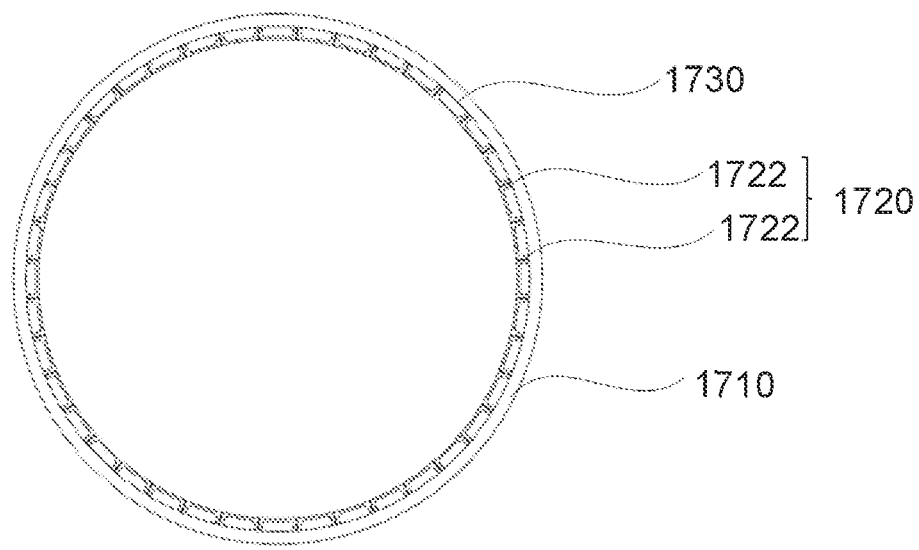
FIG. 18 is a section view illustrating an exemplary coil assembly according to some embodiments of the present disclosure.

FIG. 17 is a schematic diagram illustrating an exemplary coil assembly according to some embodiments of the present disclosure. FIG. 18 is a section view illustrating the exemplary coil assembly 1700 according to some embodiments of the present disclosure.

As shown in FIG. 17 and FIG. 18, the coil assembly 1700 may include an RF coil 1710, a second supporting assembly 1720, and a plurality of accommodating components 1730. The second supporting assembly 1720 may include a plurality of supporting units 1722 arranged along a circumferential direction of the RF coil 1710. The plurality of accommodating components 1730 may be arranged along the circumferential direction of the RF coil 1710. Each of the plurality of accommodating components 1730 may be located between the RF coil 1610 and at least a portion of one of the plurality of supporting units 1722. In some embodiments, the coil assembly 1700 may include a plurality of dielectric components (not shown in FIG. 17 and FIG. 18). The plurality of accommodating components 1730 may be configured to accommodate the plurality of dielectric components. The second supporting assembly 1720 may be configured to support the plurality of dielectric components. The plurality of dielectric components may be configured to adjust a distribution of a magnetic field (B1) generated by the coil assembly 1700.

Figure 19:
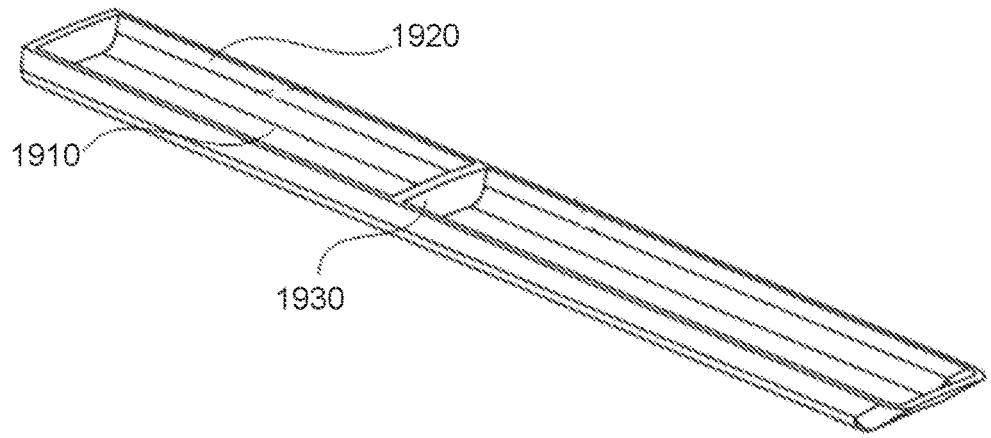
FIG. 19 is a schematic diagram illustrating an exemplary accommodating component according to some embodiments of the present disclosure.

FIG. 19 is a schematic diagram illustrating an exemplary accommodating component according to some embodiments of the present disclosure.

As shown in FIG. 19, the accommodating component 1900 may include an accommodating base 1910 (e.g., a plate), a second limiting piece 1920, and a separating piece 1930. The second limiting piece 1920 may surround the accommodating component 1900. The accommodating base 1910 and the second limiting piece 1920 may form a cavity. In some embodiments, the cavity may be used to accommodate at least one of a plurality of dielectric components. For example, the second limiting piece 1920 may include four portions surrounding four sides of the accommodating component 1900 and form a cavity with an open top. In some embodiments, the separating piece 1930 may divide the cavity into a plurality of sub-cavities. At least a portion of the plurality of sub-cavities may be selected to employ at least one of the plurality of dielectric components.

Figure 20:
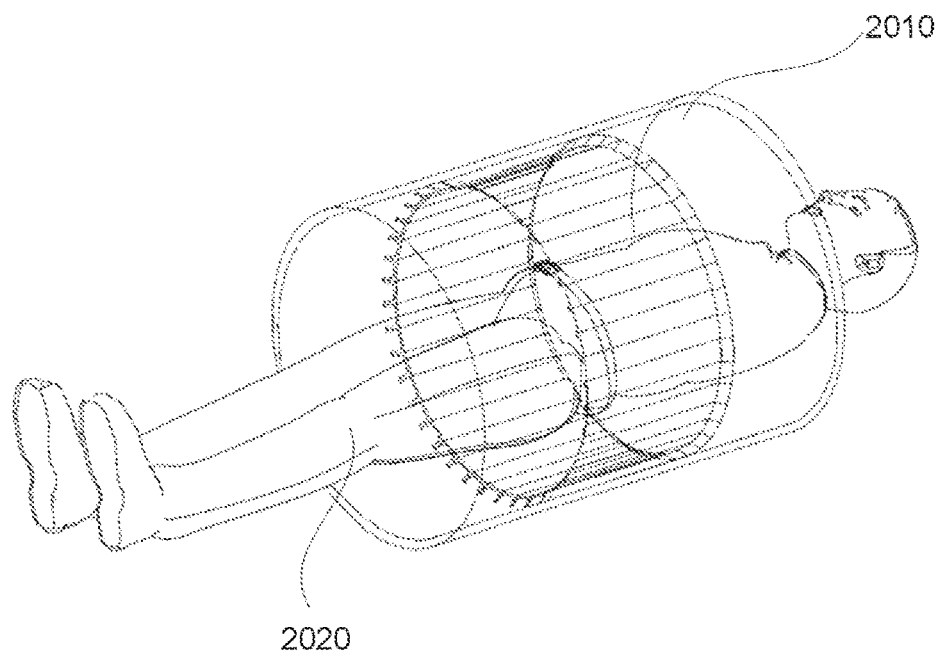
FIG. 20 is a schematic diagram illustrating an exemplary application scenario of a coil assembly according to some embodiments of the present disclosure.

FIG. 20 is a schematic diagram illustrating an exemplary application scenario of a coil assembly according to some embodiments of the present disclosure.

As shown in FIG. 20, a coil assembly 2010 may surround an object 2020. The object 2020 may be placed in a cavity of the coil assembly 2010. The coil assembly 2010 may be configured to generate a magnetic field ($B_1$). The magnetic field ($B_1$) may be applied to excite nuclear spins inside the object 2020, and an image of the object 2020 may be generated based on an MR signal determined based on the nuclear spins.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate $\pm 1\%$, $\pm 5\%$, $\pm 10\%$, or $\pm 20\%$ variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A coil assembly, comprising:
a supporting assembly, a shape of the supporting assembly being a hollow cylinder; and
a volume transmit coil supported on the supporting assembly, the volume transmit coil having at least eight coil loops and at least eight transmission ports, each of the at least eight coil loops sharing a common side with at least one adjacent coil loop, and the common side having at least one decoupling capacitor connected therein, wherein
at least one of the at least eight transmission ports is operably connected to a single coil loop of the at least eight coil loops;
each of the at least eight transmission ports is configured to transmit a drive signal to one of the at least eight coil loops for generating a magnetic field; and
an amplitude and a phase of the drive signal transmitted by the each of the at least eight transmission ports are set independently.

2. The coil assembly of claim 1, wherein the at least eight transmission ports are arranged along a circumferential direction of the volume transmit coil or a circumferential direction of the supporting assembly.

3. The coil assembly of claim 1, further comprising a plurality of electrical components supported on the supporting assembly, wherein
one of the plurality of electrical components is operably connected to one of the at least eight transmission ports; and
the one of the plurality of electrical components is configured to generate the drive signal.

4. The coil assembly of claim 3, wherein the plurality of electrical components are arranged along a circumferential direction of the volume transmit coil or a circumferential direction of the supporting assembly.

5. The coil assembly of claim 3, wherein
at least one of the plurality of electrical components includes a cable and a cable trap;
a first end of the cable is operably connected to one of the at least eight transmission ports for transmitting the drive signal; and
the cable trap is configured to define a frequency of the drive signal.

6. The coil assembly of claim 5, wherein
a second end of the cable leads to a second transmission port, and
the second transmission port is configured to transmit a power to the cable.

7. The coil assembly of claim 6, wherein
a plurality of second transmission ports corresponding to the plurality of electrical components are aggregated in a cable group; and
the cable group is located on an end of the supporting assembly along an axial direction of the supporting assembly.

8. The coil assembly of claim 6, further comprising a second electrical component configured for power supply of the volume transmit coil, wherein
the second electrical component includes a second cable;
a first end of the second cable is operably connected to the volume transmit coil; and
the second cable is configured to transmit a signal for the power supply of the volume transmit coil.

9. The coil assembly of claim 8, wherein a second end of the second cable and the second end of the cable are on opposite ends along an axial direction of the supporting assembly.

10. The coil assembly of claim 1, further comprising at least one tuning component located along a circumferential direction of the supporting assembly, wherein
the at least one tuning component is configured to adjust a resonance frequency of the volume transmit coil; and
at least one adjustment portion of the at least one tuning component is located on a first end of the supporting assembly along an axial direction of the supporting assembly.

11. The coil assembly of claim 10, further comprising at least one coupling component located along the circumferential direction of the supporting assembly, wherein
the at least one coupling component is configured to adjust a coupling degree between the at least eight coil loops; and
at least one adjustment portion of the at least one coupling component is located on a second end of the supporting assembly along the axial direction of the supporting assembly.

12. The coil assembly of claim 11, wherein one of the at least one tuning component includes a tuning rod and a tuning capacitor.

13. The coil assembly of claim 12, wherein one of the at least one coupling component includes a coupling rod and a coupling capacitor.

14. The coil assembly of claim 13, wherein
the supporting assembly includes at least one recess, and
the at least one recess is configured to accommodate at least one of the at least one tuning capacitor or the at least one coupling capacitor.

15. The coil assembly of claim 1, further comprising:
a plurality of dielectric components located between an antenna of the volume transmit coil and an object associated with coil assembly; and
a plurality of accommodating components configured to support the plurality of dielectric components.

16. The coil assembly of claim 15, further comprising:
a second supporting assembly located inside or outside the volume transmit coil;
the second supporting assembly includes a plurality of containers; and
the plurality of accommodating components located on the plurality of containers.

17. The coil assembly of claim 15, wherein
at least a portion of the plurality of accommodating components are employed for positioning the plurality of dielectric components based on a reference distribution of a reference aggregated magnetic field formed by a plurality of reference magnetic fields each of which is generated based on one of at least eight reference coil loops of a reference coil assembly.

18. The coil assembly of claim 1, wherein sizes of at least two of the at least eight coil loops are different.

19. The coil assembly of claim 18, wherein a size of each of the at least eight coil loops is set according to at least one of a distance between at least a portion of the coil loop and a portion of an object associated with the coil assembly or a reference distribution of a reference aggregated magnetic field formed by a plurality of reference magnetic fields each of which is generated based on one of at least eight reference coil loops of a reference coil assembly.

20. A magnetic resonance system, comprising at least one coil assembly, wherein each of the at least one coil assembly includes:
- a supporting assembly, a shape of the supporting assembly being a hollow cylinder; and
- a volume transmit coil supported on the supporting assembly, the volume transmit coil having at least eight coil loops and at least eight transmission ports, each of the at least eight coil loops sharing a common side with at least one adjacent coil loop, and the common side having at least one decoupling capacitor connected therein, wherein at least one of the at least eight transmission ports is operably connected to a single coil loop of the at least eight coil loops;

each of the at least eight transmission ports is configured to transmit a drive signal to one of the at least eight coil loops for generating a magnetic field; and an amplitude and a phase of the drive signal transmitted by the each of the at least eight transmission ports are set independently.

* * * * *